(12) United States Patent
Jeong et al.

(10) Patent No.: US 11,375,930 B2
(45) Date of Patent: Jul. 5, 2022

(54) ELECTRONIC DEVICE FOR SENSING BIOMETRIC INFORMATION AND CONTROL METHOD THEREOF

(71) Applicant: Samsung Electronics Co., Ltd., Suwon-si (KR)

(72) Inventors: Injo Jeong, Suwon-si (KR); Hyunguk Yoo, Suwon-si (KR); Kunkook Park, Suwon-si (KR); Seungeun Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 685 days.

(21) Appl. No.: 16/265,340

(22) Filed: Feb. 1, 2019

(65) Prior Publication Data

US 2019/0231235 A1 Aug. 1, 2019

(30) Foreign Application Priority Data

Feb. 1, 2018 (KR) .................. 10-2018-0013048

(51) Int. Cl.
*A61B 5/1486* (2006.01)
*G16H 50/20* (2018.01)
(Continued)

(52) U.S. Cl.
CPC ............ *A61B 5/1486* (2013.01); *A61B 5/002* (2013.01); *A61B 5/0533* (2013.01);
(Continued)

(58) Field of Classification Search
CPC ....... A61B 5/1486; A61B 5/282; A61B 5/681; A61B 5/0533; A61B 5/14532;
(Continued)

(56) References Cited

U.S. PATENT DOCUMENTS 8,116,841 B2 2/2012 Bly et al.
8,249,686 B2 8/2012 Libbus et al.
(Continued)

FOREIGN PATENT DOCUMENTS

CN 105615881 A 6/2016
JP 2012-011208 A 1/2012
(Continued)

OTHER PUBLICATIONS

International Search Report dated May 23, 2019, issued in International Patent Application No. PCT/KR2019/001241.
(Continued)

*Primary Examiner* — Allen Porter
*Assistant Examiner* — Abid A Mustansir
(74) *Attorney, Agent, or Firm* — Jefferson IP Law, LLP

(57) ABSTRACT

An electronic device for obtaining biometric information is provided. The electronic device includes at least one communication circuit, a first pad including a first electrode and a second electrode, the first electrode being coated with a catalyst associated with first biometric information, a second pad including at least a third electrode, and a processor for controlling the at least one communication circuit, the first pad, and the second pad. The processor is configured to obtain the first biometric information, based at least on an electric current generated by applying a specified voltage between the first electrode and the second electrode and obtain second biometric information, based at least on a voltage difference between the second electrode and the third electrode.

16 Claims, 17 Drawing Sheets

(51) Int. Cl.
    *A61B 5/00*     (2006.01)
    *A61B 5/145*     (2006.01)
    *A61B 5/16*     (2006.01)
    *A61B 5/0533*     (2021.01)
    *H04B 1/3827*     (2015.01)
    *A61B 5/282*     (2021.01)
    *A61B 5/0537*     (2021.01)
    *A61B 5/0205*     (2006.01)
    *G16H 40/67*     (2018.01)
    *A61B 5/0245*     (2006.01)
    *A61B 5/318*     (2021.01)

(52) U.S. Cl.
    CPC ...... *A61B 5/14532* (2013.01); *A61B 5/14546* (2013.01); *A61B 5/165* (2013.01); *A61B 5/282* (2021.01); *A61B 5/443* (2013.01); *A61B 5/681* (2013.01); *A61B 5/6833* (2013.01); *A61B 5/68335* (2017.08); *A61B 5/725* (2013.01); *A61B 5/742* (2013.01); *G16H 50/20* (2018.01); *H04B 1/385* (2013.01); *A61B 5/0022* (2013.01); *A61B 5/0205* (2013.01); *A61B 5/0245* (2013.01); *A61B 5/0537* (2013.01); *A61B 5/318* (2021.01); *A61B 5/746* (2013.01); *A61B 2562/0215* (2017.08); *G16H 40/67* (2018.01)

(58) Field of Classification Search
    CPC ..... A61B 5/14546; A61B 5/725; A61B 5/742; A61B 5/6833; A61B 5/165; A61B 5/433; A61B 5/0022; A61B 5/318; A61B 5/0205; A61B 5/746; A61B 5/0245; A61B 5/0537; A61B 5/7225; A61B 5/24; G16H 50/20
    See application file for complete search history.

(56) References Cited

U.S. PATENT DOCUMENTS

| | | | |
|---|---|---|---|
| 8,285,356 B2 | 10/2012 | Bly et al. | |
| 8,389,428 B2 | 3/2013 | Wada et al. | |
| 8,591,430 B2 | 11/2013 | Amurthur et al. | |
| 8,613,708 B2 | 12/2013 | Bishay et al. | |
| 8,688,190 B2 | 4/2014 | Libbus et al. | |
| 8,795,174 B2 | 8/2014 | Manicka et al. | |
| 8,818,481 B2 | 8/2014 | Bly et al. | |
| 9,144,387 B2 | 9/2015 | Ko et al. | |
| 9,662,032 B2 | 5/2017 | Lee et al. | |
| 9,770,182 B2 | 9/2017 | Bly et al. | |
| RE46,926 E | 7/2018 | Bly et al. | |
| 10,028,699 B2 | 7/2018 | Libbus et al. | |
| 2002/0106709 A1* | 8/2002 | Potts | A61B 5/14532 435/14 |
| 2003/0088166 A1 | 5/2003 | Say et al. | |
| 2006/0007171 A1 | 1/2006 | Burdi et al. | |
| 2006/0118415 A1 | 6/2006 | Say et al. | |
| 2009/0076345 A1 | 3/2009 | Manicka et al. | |
| 2009/0076363 A1 | 3/2009 | Bly et al. | |
| 2009/0076364 A1 | 3/2009 | Libbus et al. | |
| 2009/0076405 A1 | 3/2009 | Amurthur et al. | |
| 2010/0204554 A1 | 8/2010 | Say et al. | |
| 2010/0292595 A1* | 11/2010 | Paul | A61B 5/332 600/509 |
| 2011/0009729 A1 | 1/2011 | Shin et al. | |
| 2011/0287264 A1 | 11/2011 | Wada et al. | |
| 2012/0089037 A1 | 4/2012 | Bishay et al. | |
| 2012/0108920 A1 | 5/2012 | Bly et al. | |
| 2012/0277549 A1 | 11/2012 | Libbus et al. | |
| 2013/0079619 A1 | 3/2013 | Lee et al. | |
| 2013/0085347 A1 | 4/2013 | Manicka et al. | |
| 2013/0204110 A1 | 8/2013 | Ko et al. | |
| 2013/0253285 A1 | 9/2013 | Bly et al. | |
| 2014/0051941 A1 | 2/2014 | Messerschmidt | |
| 2014/0288385 A1 | 9/2014 | Amurthur et al. | |
| 2014/0330088 A1 | 11/2014 | Libbus et al. | |
| 2014/0330136 A1 | 11/2014 | Manicka et al. | |
| 2015/0005589 A1 | 1/2015 | Bly et al. | |
| 2015/0057515 A1* | 2/2015 | Hagen | G01N 27/3273 600/346 |
| 2016/0331290 A1* | 11/2016 | Oh | A61B 5/0538 |
| 2017/0124350 A1* | 5/2017 | Reihman | H04W 12/033 |
| 2017/0172484 A1* | 6/2017 | Sonner | A61B 5/14539 |
| 2017/0215773 A1 | 8/2017 | Heikenfeld et al. | |

FOREIGN PATENT DOCUMENTS

| | | |
|---|---|---|
| KR | 10-2013-0033267 A | 4/2013 |
| WO | 2016/007944 A2 | 1/2016 |
| WO | 2017/173462 A1 | 10/2017 |

OTHER PUBLICATIONS

Extended European Search Report dated May 27, 2019, issued in European Patent Application No. 19154996.3.

European Office Action dated Apr. 7, 2020, issued in European Application No. 19154996.3.

European Office Action dated Nov. 25, 2019, issued in European Application No. 19154996.3.

* cited by examiner

ELECTRONIC DEVICE FOR SENSING BIOMETRIC INFORMATION AND CONTROL METHOD THEREOF

CROSS-REFERENCE TO RELATED APPLICATION(S)

This application is based on and claims priority under 35 U.S.C. § 119(a) of a Korean patent application number 10-2018-0013048, filed on Feb. 1, 2018, in the Korean Intellectual Property Office, the disclosure of which is incorporated by reference herein in its entirety.

BACKGROUND

1. Field

The disclosure relates to an electronic device for sensing biometric information and a method for controlling the electronic device.

2. Description of Related Art

With the wide use of various portable electronic devices such as smartphones, studies on methods of sensing biometric information using portable electronic devices have been conducted. Health care services for users may be provided by sensing biometric information using portable electronic devices. Various biometric information sensing methods have been studied to provide more accurate health care services. In addition, methods for providing complex health care services using more diverse biometric information have been studied.

Methods for obtaining various biometric information using biometric sensors have been studied. For example, a degree of fatigue may be measured using lactic acid. The lactic acid may be decomposed into pyruvate and hydrogen peroxide by using a lactate oxidase LOx. Thereafter, electric charges by an oxidation reaction may be generated by applying a positive potential to the hydrogen peroxide. Accordingly, the degree of fatigue may be sensed by measuring the quantity of electric charge generated by the oxidation reaction. In this case, a biometric sensor for measuring the degree of fatigue may include three electrodes. For example, the biometric sensor may measure the degree of fatigue using the quantity of electric charge generated based on a potential difference between a working electrode including a LOx layer and a reference electrode.

In another example, electrocardiography (ECG) may be measured. For example, a biometric sensor may include two to twelve electrodes and may measure a potential difference between a plurality of points that is generated by a cardiac impulse, thereby measuring ECG.

For example, in the case where a biometric sensor measures a degree of fatigue and ECG according to the related art, the biometric sensor may include at least five electrodes.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic device including a biometric sensor and a control method thereof for achieving a reduction in cost and size.

Additional aspects will be set forth in part in the description which follows and, in part, will be apparent from the description, or may be learned by practice of the presented embodiments.

In accordance with an aspect of the disclosure, an electronic device is provided. The electronic device includes at least one communication circuit, a first pad including a first electrode and a second electrode, the first electrode being coated with a catalyst associated with first biometric information, a second pad including at least a third electrode, and a processor that controls the at least one communication circuit, the first pad, and the second pad. The processor obtains the first biometric information, based at least on an electric current generated by applying a specified voltage between the first electrode and the second electrode and obtains second biometric information, based at least on a voltage difference between the second electrode and the third electrode.

In accordance with another aspect of the disclosure, a method for obtaining biometric information is provided. The method includes applying a specified voltage to a second electrode of a first pad of an electronic device and a third electrode of a second pad of the electronic device, obtaining skin moisture, based on an electric current generated between the second electrode and the third electrode by the specified voltage, and obtaining first biometric information by using a first electrode and the second electrode of the first pad, based at least on the skin moisture. The first electrode is coated with a catalyst associated with the first biometric information.

According to various embodiments of the disclosure, various types of biometric information may be measured using a small number of electrodes.

Furthermore, according to various embodiments, various types of biometric information may be measured using a replaceable pad.

In addition, the disclosure may provide various effects that are directly or indirectly recognized.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
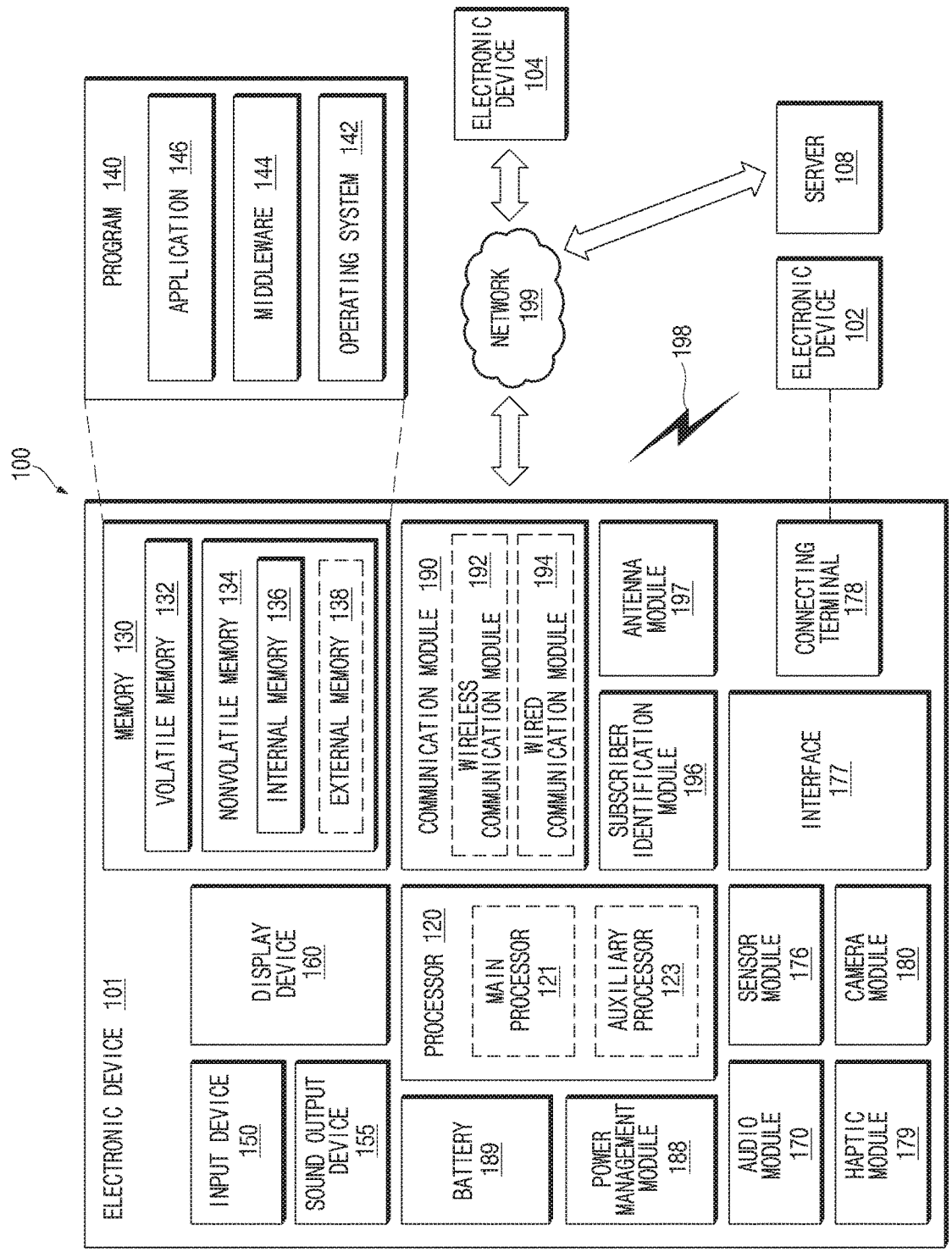
FIG. 1 is a block diagram illustrating an electronic device in a network environment according to an embodiment of the disclosure.

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modification of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terms of a singular form may include plural forms unless otherwise specified. In this disclosure, the expressions "A or B", "at least one of A or/and B", and the like may include any and all combinations of one or more of the associated listed items. The terms, such as "first", "second", and the like may be used to refer to various components regardless of the order and/or the priority and to distinguish the relevant components from other components, but do not limit the components. When a component (e.g., a first component) is referred to as being "(operatively or communicatively) coupled with/to" or "connected to" another component (e.g., a second component), the component may be directly coupled with/to or connected to the another component or may be connected through an intervening component (e.g., a third component).

According to the situation, the expression "configured to" used in the disclosure may be interchangeably used as, for example, the expression "suitable for", "having the capacity to", "adapted to", "made to", or "designed to" in hardware or software. In another situation, the expression "a device configured to" may mean that the device is "capable of" operating together with another device or other parts. For example, a "processor configured to (or set to) perform A, B, and C" may mean a dedicated processor (e.g., an embedded processor) for performing a corresponding operation or a generic-purpose processor (e.g., a central processing unit (CPU) or an application processor (AP)) which performs corresponding operations by executing one or more software programs which are stored in a memory device.

An electronic device according to various embodiments of the disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group phase 1 or phase 2 (MPEG-1 or MPEG-2) audio layer 3 (MP3) players, medical devices, cameras, or wearable devices. The wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable circuit. According to various embodiments, the electronic device may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media boxes (e.g., Samsung HomeSync™, Apple TV™, and Google TV™), game consoles (e.g., Xbox™ and PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, global navigation satellite system (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, drones, automatic teller machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like). According to an embodiment, the electronic device may include at least one of parts of furniture, buildings/structures, or automobiles, electronic boards, electronic signature receiving devices, projectors, or various measuring instruments (e.g., water meters, electricity meters, gas meters, or wave meters, and the like). According to various embodiments, the electronic device may be a flexible electronic device or may be a combination or two or more of the above-described devices. An electronic device according to an embodiment of the disclosure may not be limited to the above-described electronic devices. In this disclosure, the term "user" may refer to a person who uses an electronic device or may refer to a device (e.g., an artificial intelligence electronic device) that uses the electronic device.

FIG. 1 is a block diagram illustrating an electronic device 101 in a network environment 100 according to various embodiments of the disclosure.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a CPU or an AP), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an ISP or a CP) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture an image or moving images. According to an embodiment, the camera module 180 may include one or more lenses, image sensors, ISPs, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently from the processor 120 (e.g., the AP) and supports a direct (e.g., wired) communication or a wireless communication. According to an embodiment, the communication module 190 may include a wireless communication module 192 (e.g., a cellular communication module, a short-range wireless communication module, or a GNSS communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or the server 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Various operations of the electronic device 101, which will be described below, may be performed by the processor 120. For example, the processor 120 may control the operations of the electronic device 101, based on instructions stored in the memory 130.

Figure 2:
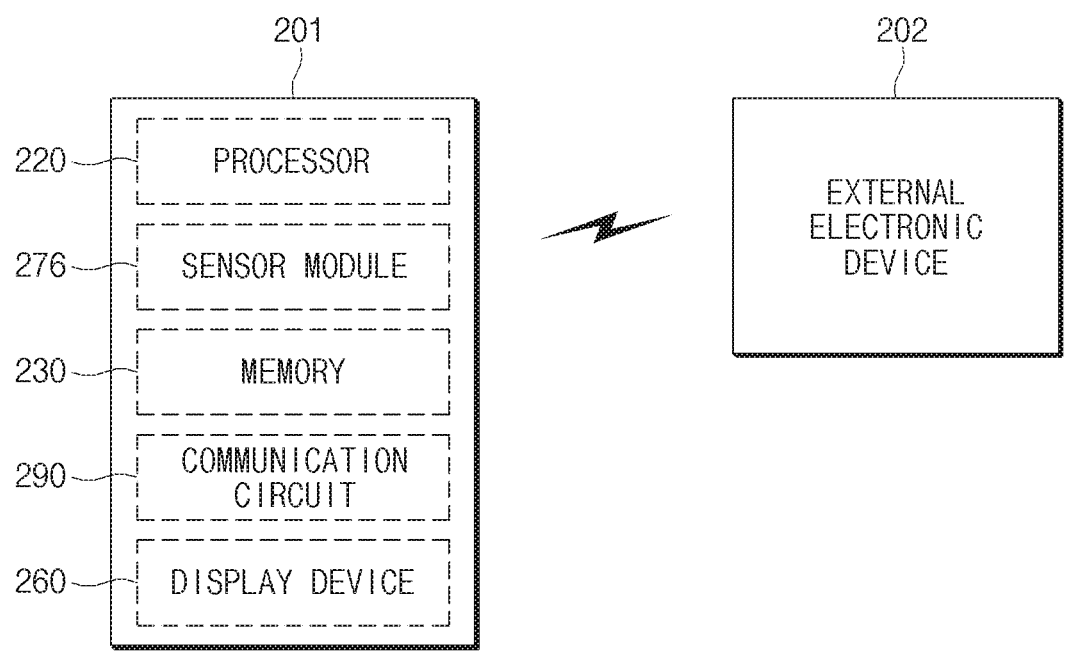
FIG. 2 is a block diagram illustrating an electronic device for sensing biometric information, according to an embodiment of the disclosure.

FIG. 2 is a block diagram illustrating an electronic device 201 according to various embodiments of the disclosure.

Referring to FIG. 2, the electronic device 201 (e.g., the electronic device 101 of FIG. 1) may include at least one of a processor 220 (e.g., the processor 120 of FIG. 1), a memory 230 (e.g., the memory 130 of FIG. 1), a sensor module 276 (e.g., the sensor module 176 of FIG. 1), a communication circuit 290 (e.g., the communication module 190 of FIG. 1), or a display device 260 (e.g., the display device 160 of FIG. 1).

The processor 220 may be operatively coupled with at least one of the memory 230, the sensor module 276, the communication circuit 290, or the display device 260 and may control operations of the electronic device 201 and/or the components of the electronic device 201.

The memory 230 may be operatively coupled with the processor 220 and may store commands for controlling the processor 220. The memory 230 may store commands for causing the processor 220 to perform operations of the processor 220 or the electronic device 201, which will be described below.

According to an embodiment of the present disclosure, the memory 230 may store biometric information measured by the sensor module 276. According to another embodiment, the memory 230 may store reference values (e.g., a reference table) that are compared with the biometric information. For example, the memory 230 may store a table that represents a relationship between the quantity of electric charge (e.g., electric current) and a lactate concentration or a degree of fatigue. In another example, the memory 230 may store a table that represents a relationship between the quantity of electric charge and a glucose concentration or blood glucose.

The memory 230 may store user profile information or initial setting information. For example, the memory 230 may store measurement values associated with a user profile. The user profile information may be received from an external electronic device 202. The user profile may include, for example, a user name, an ID, an age, a birth data, a height, and/or a weight.

The communication circuit 290 may provide wired or wireless communication with the external electronic device 202 (e.g., an electronic device, such as a smartphone, which includes a display) via a network. For example, the communication circuit 290 may provide the communication with the external electronic device 202 using at least one of short-range wireless communication (e.g., near field communication (NFC), Wi-Fi, Zigbee, Z-wave, Bluetooth, or Bluetooth low energy (BLE)). In another example, the communication circuit 290 may provide the communication with the external electronic device 202 using wireless communication such as cellular communication. The communication circuit 290 may transmit information stored in the memory 230 to the external electronic device 202, or may receive information from the external electronic device 202, under the control of the processor 220.

The display device 260 may display a status of the electronic device 201, notification, and/or sensing information according to instructions of the processor 220. According to an embodiment of the present disclosure, the display device 260 may include a plurality of light emitting diodes (LEDs). For example, the display device 260 may display a power status of the electronic device 201, a sensing mode of the electronic device 201, and/or notification information by using on/off of the LEDs, colors of the LEDs, and/or the number of turned-on LEDs. According to another embodiment, the display device 260 may include at least one display (e.g., a liquid crystal display (LCD), an LED display, and/or an organic LED (OLED) display).

The sensor module 276 may include one or more electrodes for measuring a plurality of biometric information and/or environmental information. According to an embodiment of the present disclosure, the sensor module 276 may include at least one electrode for measuring at least one of fatigue, blood glucose, electrocardiography (ECG), galvanic skin reflex (GSR), grip, temperature, or humidity. The sensor module 276 may include a pad that includes at least one electrode and makes contact with a user's skin, or may be coupled with a detachable pad or a detachable patch pad. According to another embodiment, the sensor module 276 may further include at least one sensor for sensing user information. For example, the sensor module 276 may include a photoplethysmography (PPG) sensor, a gas sensor, and/or an acceleration sensor.

The configuration of the electronic device 201 illustrated in FIG. 2 is illustrative, and the electronic device 201 is not limited thereto. For example, the electronic device 201 may not include at least one of the components illustrated in FIG. 2, or may further include at least one component not being illustrated in FIG. 2. For example, the electronic device 201 may further include a user interface (e.g., at least one button) for receiving a user input and/or a battery. In another example, the electronic device 201 may further include a voltage application device (e.g., a PMIC) for applying voltage to an electrode and/or a current/voltage measurement device. In another example, the electronic device 201 may include an analog-to-digital converter (ADC) or an analog front end (AFE) for receiving/modulating an analog signal received from the sensor module 276.

The electronic device 201 may include a user interface that includes at least one button. For example, the user interface may include a button for controlling the power of the electronic device 201 and a button for selecting a measurement mode.

The processor 220 may obtain at least one piece of biometric information using the sensor module 276 in response to a user input. For example, the processor 220 may receive raw data from the sensor module 276 and may obtain biometric information (e.g., blood glucose or a degree of fatigue) that corresponds to the raw data, by using a value stored in the memory 230. For example, the processor 220 may obtain the raw data by applying a specified voltage to the sensor module 276 and measuring the quantity of electric charge (e.g., electric current) using the sensor module 276.

The processor 220 may provide the obtained biometric information to the user. For example, the processor 220 may display the biometric information on the display device 260. In another example, the processor 220 may transmit the biometric information to the external electronic device 202 via the communication circuit 290. The external electronic device 202 may display the received biometric information on the display. For example, the biometric information may be displayed using a number and/or a graphic element (e.g., a graph).

The processor 220 may provide notification to the user when the biometric information obtained satisfies a specified condition. For example, the processor 220 may provide the notification using the display device 260 or another output means (e.g., a sound or tactile output means) of the electronic device 201. In another example, the processor 220 may transmit notification information to the external electronic device 202 to provide the notification using the external electronic device 202.

According to various embodiments, the electronic device 201 may include at least one communication circuit (e.g., the communication circuit 290), a first pad including a second electrode and a first electrode coated with a catalyst associated with first biometric information, a second pad including at least a third electrode, and the processor 220 configured to control the at least one communication circuit, the first pad, and the second pad. For example, the sensor module 276 may include the first pad and the second pad. The processor 220 may be configured to obtain the first biometric information, based at least on an electric current generated by applying a specified voltage between the first electrode and the second electrode and obtain second biometric information based at least on a voltage difference between the second electrode and the third electrode.

The processor 220 may be configured to obtain the first biometric information by using the first electrode as a working electrode and the second electrode as a reference electrode and a counter electrode.

The first biometric information may include at least one of a lactate concentration or a degree of fatigue, and the catalyst may include a lactate oxidase.

The first biometric information may include at least one of a glucose concentration or blood glucose, and the catalyst may include a glucose oxidase.

The first pad and the second pad may include an electrolyte layer containing an ion-conducting material.

The processor 220 may be configured to apply a specified voltage between the second electrode and the third electrode and obtain third biometric information, based on an electric current between the second and third electrodes to which the specified voltage is applied.

The processor 220 may obtain the second biometric information or the third biometric information, based on a user input, and the user input may be received from the external electronic device 202 via the at least one communication circuit 290, or may be received through the user interface of the electronic device 201.

The second electrode and the third electrode may be formed of a metallic material, a conductive polymer, or a transparent conductive material. The metallic material may include platinum, gold, silver, silver chloride, copper, or stainless steel. The conductive polymer may include polyacetylene, polypyrrole, polythiophene, polyphenylene, polyphenyl, or poly(3,4-ethylenedioxythiophene) (PEDOT). The transparent conductive material may include indium tin oxide (ITO), aluminum-doped zinc oxide (AZO), tin (II) oxide (SnO), or fluorine-doped tin oxide (FTO).

The processor 220 may be configured to transmit at least one of the first biometric information, the second biometric information, or the third biometric information to the external electronic device 202 via the at least one communication circuit 290.

The at least one communication circuit 290 may be configured to provide communication between the electronic device 201 and the external electronic device 202 via a short-range wireless network, and the short-range wireless network may include at least one of NFC, Bluetooth, BLE, Zigbee, or Z-wave.

The electronic device 201 may further include a low pass filter (LPF), and the LPF may be disposed between the second electrode and the third electrode.

The processor 220 may be configured to obtain the first biometric information when a specified condition is satisfied, and the specified condition may include skin moisture that is greater than or equal to a specified value.

The processor 220 may be configured to apply a specified voltage to the second electrode and the third electrode and obtain the skin moisture, based on an electric current between the second electrode and the third electrode.

The second pad may further include a fourth electrode, and the processor 220 may be configured to sense at least one of temperature, humidity, or grip using the fourth electrode.

The first pad and the second pad may be detachably equipped to the electronic device 201.

The processor 220 may be configured to provide notification when the first biometric information satisfies a first condition specified or the second biometric information satisfies a second condition specified. The first condition may include the first biometric information outside a first range specified, and the second condition may include the second biometric information outside a second range specified.

The processor 220 may be configured to provide the notification through the display device 260 of the electronic device 201 or by using the external electronic device 202. The operations of the electronic device 201 have been described above with reference to FIG. 2, with the description focused on the logical components of the electronic device 201. Hereinafter, physical components of the electronic device 201 will be described with reference to FIG. 3.

Figure 3:
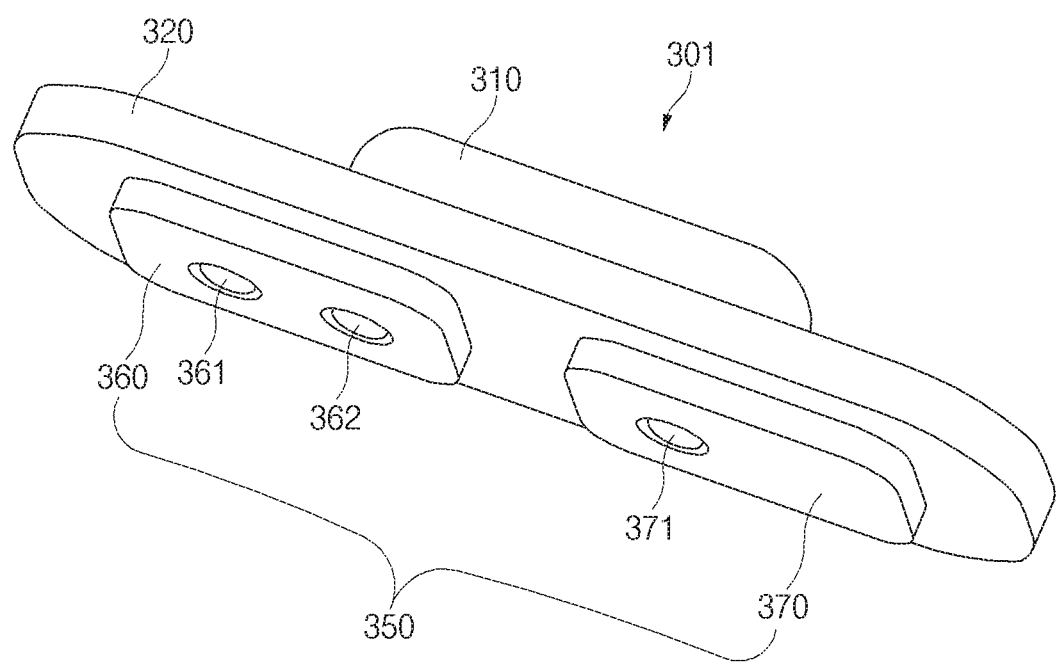
FIG. 3 is a schematic view illustrating an electronic device according to an embodiment of the disclosure.

FIG. 3 is a schematic view illustrating an electronic device 301 according to an embodiment of the disclosure.

Referring to FIG. 3, the electronic device 301 (e.g., the electronic device 201) may include at least one of an upper body 310, a main body 320, or a lower pad 350.

According to an embodiment, the upper body 310 may include at least one of the display device 260 or a user interface (not illustrated). The main body 320 may be located below the upper body 310 and may contain various components of the electronic device 301, together with the upper body 310. For example, the upper body 310 and/or the main body 320 may contain at least one of the display device 260, the communication circuit 290, the processor 220, the memory 230, or the battery. For example, the upper body 310 and the main body 320 may contain a printed circuit board (PCB) on which at least one of the display device 260, the communication circuit 290, the processor 220, the memory 230, or the battery is mounted.

The lower pad 350 (e.g., the sensor module 276) may be located below the main body 320 and may be implemented with a composite electrode in a patch pad form that includes a plurality of pads. For example, the lower pad 350 may include a first pad 360 and a second pad 370. The lower pad 350 may be detachably combined with the main body 320. For example, the type of biometric information sensed by the electronic device 301 may be changed by changing at least one pad (e.g., the first pad 360 and/or the second pad 370). The lower pad 350 may include two or more pads.

The first pad 360 and the second pad 370 may include an adhesive surface at the bottom thereof. Although the first pad 360 and the second pad 370 in FIG. 3 have adhesive surfaces separated from each other, the first pad 360 and the second pad 370 may have the same connected adhesive surface.

The first pad 360 may include at least one of a first electrode 361 and a second electrode 362. The second pad 370 may include a third electrode 371. The configurations of the first pad 360 and the second pad 370 are not limited to those illustrated in FIG. 3. For example, the second pad 370 may include a plurality of electrodes. In another example, the first pad 360 may include two or more electrodes.

The electronic device 301 (e.g., the processor 220) may obtain first biometric information (e.g., a degree of fatigue or blood glucose) by using the first electrode 361 as a working electrode and the second electrode 362 as a counter electrode and a reference electrode. For example, the electronic device 301 may control voltage to be applied, by using an operational amplifier (OP-Amp) or a regulator.

The electronic device 301 may measure a degree of fatigue using the first electrode 361 and the second electrode 362. For example, the first electrode 361 may be coated with a catalyst for reaction with lactic acid. For example, the first electrode 361 may include a reaction layer with a metal layer coated with LOx. The second electrode 362 may be formed of at least one of a metallic material (e.g., platinum, gold, silver, silver chloride, copper, or stainless steel), a conductive polymer (e.g., polyacetylene, polypyrrole, polythiophene, polyphenylene, polyphenyl, or poly(3,4-ethylenedioxythiophene) (PEDOT)), or a transparent conductive material (e.g., indium tin oxide (ITO), aluminum-doped zinc oxide (AZO), tin (II) oxide (SnO), or fluorine-doped tin oxide (FTO)). According to an embodiment, the electronic device 301 may measure a degree of fatigue by applying a specified voltage (e.g., about 0.5 V to about 2 V) between the first electrode 361 and the second electrode 362 and measuring the quantity of electric charge (e.g., electric current) through the second electrode 362. In this case, the first electrode 361 may operate as a working electrode, and the second electrode 362 may operate as a counter electrode and a reference electrode.

The first pad 360 and/or the second pad 370 may include an electrolyte layer to sense biometric information (e.g., the first biometric information and/or the second biometric information). For example, the electrolyte layer may contain ions such as a sodium ion ($Na^+$), a chloride ion ($Cl^-$), and the like. The first electrode 361 and the second electrode 362 may constitute one electric circuit that includes the electrolyte layer of the first pad 360.

The electronic device 301 may obtain a lactate concentration or a degree of fatigue that corresponds to the quantity of electric charge sensed through the first electrode 361 and the second electrode 362, by using an electric charge-lactate concentration table or an electric charge-fatigue table that is stored in the memory 230. For example, the electronic device 301 may store the obtained lactate concentration or the obtained degree of fatigue in the memory 230 every specified period (e.g., about one minute to about ten minutes). In another example, the electronic device 301 may transmit the obtained lactate concentration or the obtained degree of fatigue to the external electronic device 202 every specified period (e.g., about one minute to about ten minutes).

The processor 220 may provide a warning to a user when the lactate concentration or the degree of fatigue satisfies a first condition (e.g., when the lactate concentration or the degree of fatigue is outside a specified range). For example, the processor 220 may provide notification (e.g., a warning) using the display device 260 or the external electronic device 202. In another example, the processor 220 may provide notification using a component of the electronic device 201, or a component of the external electronic device 202, for providing sound and/or tactile notification. The processor 220 may generate an interrupt to generate the warning.

The electronic device 301 may measure blood glucose using the first electrode 361 and the second electrode 362. The first electrode 361 may include a reaction layer containing a glucose oxidase GOx for selective reaction with glucose. For example, the reaction layer may be coated on the surface of at least part of a metal layer of the first electrode 361. The second electrode 362 may be formed of at least one of a metallic material (e.g., platinum, gold, silver, silver chloride, copper, or stainless steel), a conductive polymer (e.g., polyacetylene, polypyrrole, polythiophene, polyphenylene, polyphenyl, or poly(3,4-ethylenedioxythiophene) (PEDOT)), or a transparent conductive material (e.g., indium tin oxide (ITO), aluminum-doped zinc oxide (AZO), tin (II) oxide (SnO), or fluorine-doped tin oxide (FTO)). The electronic device 301 may measure the blood glucose by applying a specified voltage (e.g., about 0.5 V to about 2 V) between the first electrode 361 and the second electrode 362 and measuring the quantity of electric charge (e.g., electric current) through the second electrode 362. For example, the first electrode 361 may operate as a working electrode, and the second electrode 362 may operate as a counter electrode and/or a reference electrode.

To sense first biometric information, the first pad 360 may include an electrolyte layer that electrically couples the first electrode 361 and the second electrode 362. To sense second biometric information, the first pad 360 and the second pad 370 may include an electrolyte layer. For example, the electrolyte layer may facilitate detection of biometric information (e.g., the first biometric information and/or the second biometric information) by increasing the magnitude of an electrical signal (e.g., current and/or voltage) between the electrodes (the first electrode 361, the second electrode 362, and/or the third electrode 371). For example, the electrolyte layer may contain various ions (e.g., a sodium ion and/or a chloride ion). When the first electrode 361 and the second electrode 362 are used to measure blood glucose, a positive oxidation potential may flow through the first electrode 361, and a negative reduction potential may flow through the second electrode 362.

The electronic device 301 may obtain a glucose concentration or blood glucose that corresponds to the quantity of electric charge sensed through the first electrode 361 and the second electrode 362, by using an electric charge-glucose concentration table or an electric charge-blood glucose table that is stored in the memory 230. For example, the electronic device 301 may store the obtained glucose concentration or the obtained blood glucose in the memory 230 every specified period (e.g., about one minute to about ten minutes). In another example, the electronic device 301 may transmit the obtained glucose concentration or the obtained blood glucose to the external electronic device 202 every specified period (e.g., about one minute to about ten minutes).

The processor 220 may provide notification (e.g., a warning) to the user when the glucose concentration or the blood glucose satisfies a first condition (e.g., when the glucose concentration or the blood glucose is outside a specified range).

The electronic device 301 may measure second biometric information (e.g., ECG) and third biometric information (e.g., GSR) using the second electrode 362 and the third electrode 371. The electronic device 301 may measure the second biometric information (e.g., ECG), based on a voltage difference between the second electrode 362 and the third electrode 371. The electronic device 301 may measure the third biometric information (e.g., GSR), based on an electric current between the second electrode 362 and the third electrode 371. For example, the third electrode 371 may be formed of a metallic material (e.g., platinum, gold, silver, silver chloride, copper, or stainless steel), a conductive polymer (e.g., polyacetylene, polypyrrole, polythiophene, polyphenylene, polyphenyl, or PEDOT), or a transparent conductive material (e.g., ITO, AZO, SnO, or FTO). The third electrode 371 may be coupled to a LPF, a high pass filter (HPF), and/or a band pass filter (BPF) for removing noise.

The electronic device 301 may obtain ECG information, based on a voltage difference between the second electrode 362 and the third electrode 371. For example, the processor 220 may provide notification (e.g., a warning) when a heart rate satisfies a specified condition (e.g., when the heart rate is above or below a specified range).

The electronic device 301 may measure GSR by applying a specified voltage between the second electrode 362 and the third electrode 371 and measuring an electric current between the second electrode 362 and the third electrode 371. For example, the electronic device 301 may measure the GSR by determining a resistance value, based on the applied voltage and the measured electric current. The processor 220 may determine the current stress status, based on the measured GSR value, a variation in GSR, and/or a change trend in GSR. The processor 220 may provide notification (e.g., a warning) when the current stress status satisfies a specified condition (when the current stress status is outside a normal range).

While the second pad 370 in FIG. 3 includes only the third electrode 371, the second pad 370 may further include one or more additional electrodes according to various embodiments. For example, the second pad 370 may further include an additional electrode as a grip sensor for sensing attachment of the second pad 370. In another example, the second pad 370 may further include an additional electrode for measuring the user's body temperature or skin humidity. The third electrode 371 may be used to measure ECG, and the additional electrode may be used to measure GSR.

In the above-described embodiments, the processor 220 may provide the notification (e.g., a warning) using, for example, the display device 260 or the external electronic device 202. In another example, the processor 220 may provide the notification using a component of the electronic device 201, or a component of the external electronic device 202, for providing sound and/or tactile notification. The processor 220 may generate an interrupt to generate a warning.

In FIG. 3, the lower pad 350 may be implemented with at least one detachable patch pad. The structure of a patch pad corresponding to the first pad 360 in a detachable form is described below with reference to FIG. 4.

Figure 4:
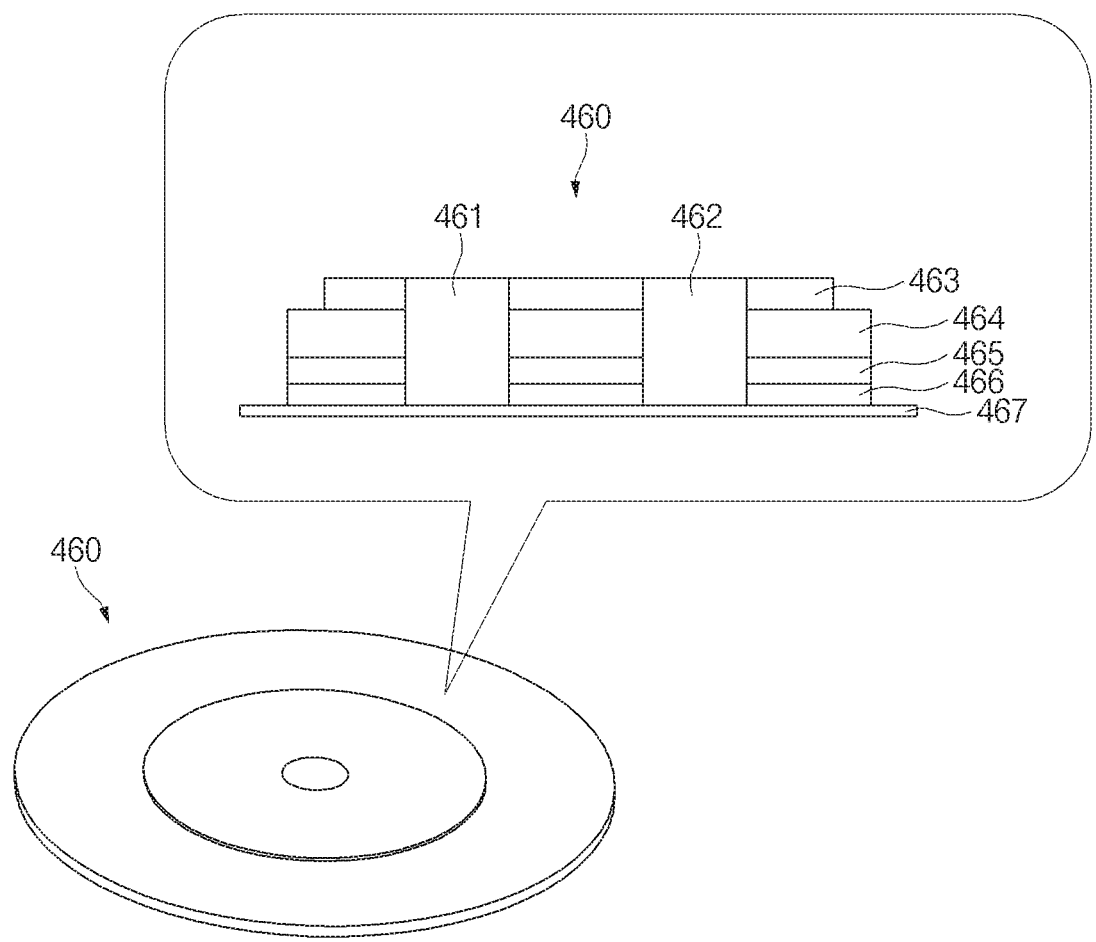
FIG. 4 is a view illustrating a configuration of a patch pad according to an embodiment of the disclosure.

FIG. 4 is a view illustrating a configuration of a patch pad according to an embodiment of the disclosure.

Referring to FIG. 4, according to various embodiments of the disclosure, the patch pad 460 may be located on a release film 467. For example, the patch pad 460 may be attached to skin using an adhesive layer 466 after removal of the release film 467. For the adhesion to the skin, the patch pad 460 may include the adhesive layer 466 (e.g., a painless adhesive). An electrolyte layer 465 may be located between the adhesive layer 466 and an upper cover 464. A gel conservation film 463 may be located at the top of the patch pad 460.

The patch pad 460 may include, in the center thereof, a first sensor unit 461 and a second sensor unit 462 that correspond to the first electrode 361 and the second electrode 362, respectively. For example, the first sensor unit 461 may contain a lactate oxidase material for reacting with lactic acid. The second sensor unit 462 may operate as a counter electrode of the first sensor unit 461 or as an electrode for measuring ECG.

The electronic device 301 may sense biometric information using a patch pad (e.g., the patch pad 460) that is coupled with at least some of the electrodes 361, 362, and 371. For example, biometric information to be sensed may be changed by changing the type of the patch pad.

Various embodiments of the disclosure are described below, based on the electronic device 301 including the patch pad that has been described above with reference to FIG. 3. However, as described above with reference to FIG. 4, a pad, which will be described below, may be implemented in a patch pad form. Specific components of an electronic device according to an embodiment of the disclosure will be described below with reference to FIG. 5.

Figure 5:
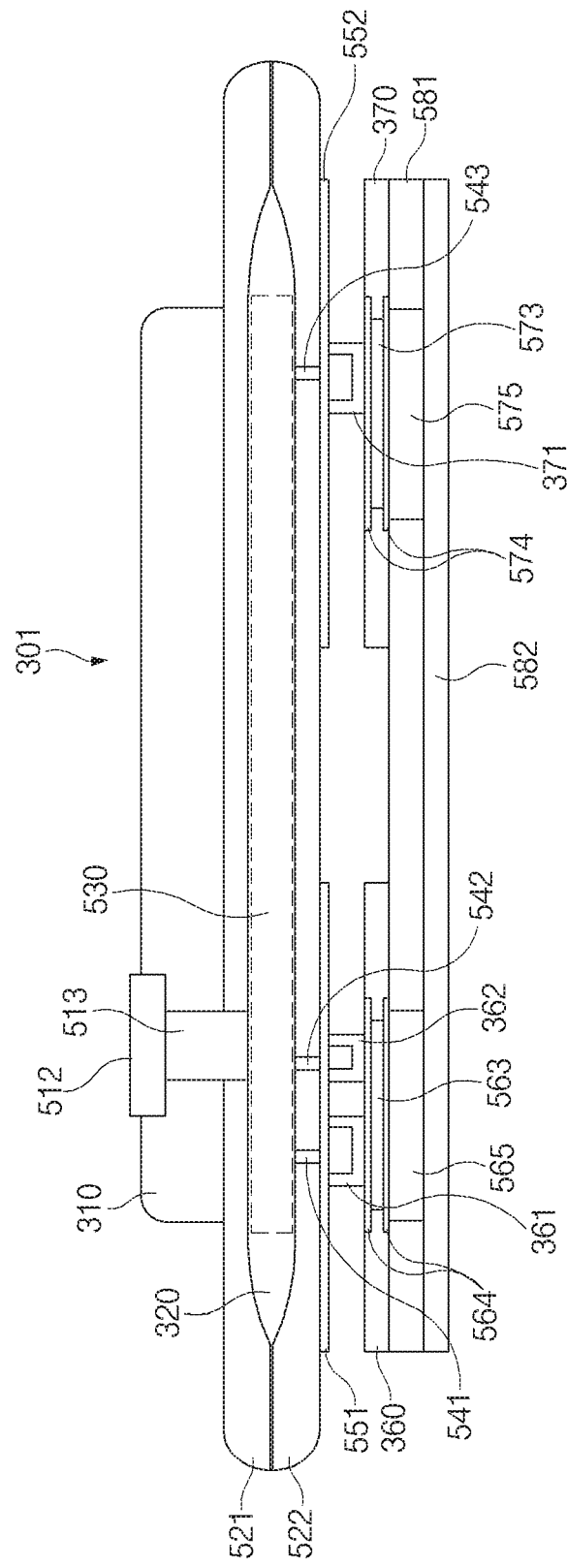
FIG. 5 is a view illustrating a configuration of an electronic device according to an embodiment of the disclosure.

FIG. 5 is a view illustrating a configuration of an electronic device according to an embodiment of the disclosure.

Referring to FIG. 5, according to various embodiments of the disclosure, a button unit 512 may be located on the upper body 310 of the electronic device 301. According to an embodiment, the button unit 512 may include one or more buttons. The button unit 512 may be electrically or physically coupled with a controller 530 in the main body 320 through a button connecting part 513. A display device (e.g., the display device 260 of FIG. 2) may be exposed through an upper surface of the upper body 310.

The main body 320 may include an upper housing 521 and a lower housing 522. For example, the upper housing 521 and the lower housing 522 may be combined together using an adhesive and/or a physical coupling means (e.g., a screw). The controller 530 may be located in the main body 320. The controller 530 may include a PCB and at least one of a battery or electronic parts (e.g., at least one of the communication circuit 290, the processor 220, a vibrating transducer, and the memory 230 of FIG. 2) mounted on the PCB.

The controller 530 may be electrically coupled with the first electrode 361, the second electrode 362, and the third electrode 371 through electrode connecting parts 541, 542, and 543.

Intermediate pads 551 and 552 may be attached to the lower housing 522. The intermediate pads 551 and 552 may provide insulation and sealing for the first electrode 361, the second electrode 362, and the third electrode 371 that protrude from the lower housing 522.

The first pad 360 may include an electrolyte layer 563 located between electrolyte conservation parts 564. The second pad 370 may include an electrolyte layer 573 located between electrolyte conservation parts 574. The first pad 360 and the second pad 370 may include measurement holes 565 and 575 located in a fixed film 581 and an adhesive part 582. While the adhesive part 582 and the fixed film 581 in FIG. 5 are each implemented with one body, the first pad 360 and the second pad 370 may include separate adhesive parts and separate fixed films according to an embodiment.

The second electrode 362 and the third electrode 371 may be electrically coupled together in the controller 530. For example, the electronic device 301 may measure ECG, based at least on a potential difference between the second electrode 362 and the third electrode 371. The electronic device 301 may measure GSR, based at least on an electric current between the second electrode 362 and the third electrode 371.

The first electrode 361 and the second electrode 362 may be electrically coupled together in the controller 530. The electronic device 301 may measure a degree of fatigue or blood glucose using the first electrode 361 and the second electrode 362. For example, the electronic device 301 may measure the degree of fatigue or the blood glucose by applying a specified voltage between the first electrode 361 and the second electrode 362 and measuring the quantity of electric charge generated from the applied voltage. The electronic device 301 may use the first electrode 361 as a working electrode and the second electrode 362 as a counter electrode and/or a reference electrode.

Figure 6:
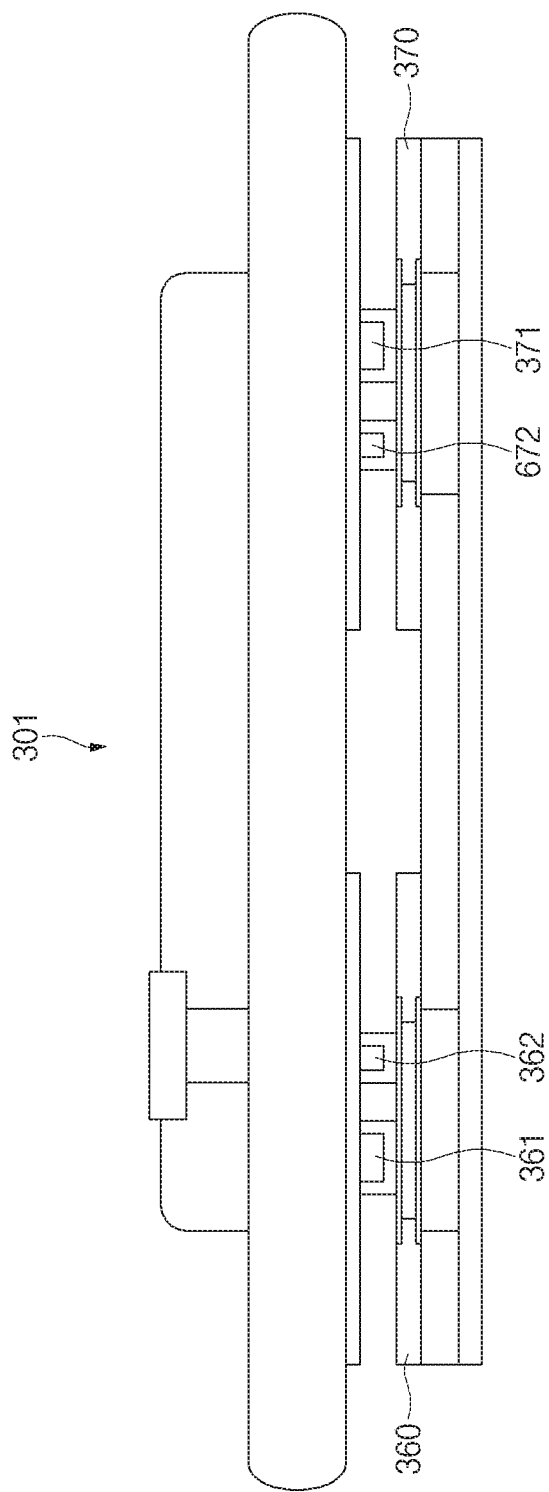
FIG. 6 is a view illustrating a configuration of an electronic device according to an embodiment of the disclosure.

FIG. 6 is a view illustrating a configuration of an electronic device according to another embodiment of the disclosure.

Referring to FIG. 6, according to an embodiment of the disclosure, the first pad 360 of the electronic device 301 may include the first electrode 361 and the second electrode 362, and the second pad 370 of the electronic device 301 may include the third electrode 371 and a fourth electrode 672. For example, the electronic device 301 of FIG. 6 may further include the fourth electrode 672, compared with the electronic device 301 of FIG. 5.

The fourth electrode 672 may include at least one of a temperature sensor, a humidity sensor, or a grip sensor. For example, the temperature sensor may include at least one of a thermocouple, a metal temperature resistor, a thermistor, an IC temperature sensor, a contact type magnetic temperature sensor, a thermopile, or a non-contact type pyroelectric temperature sensor. For example, the grip sensor may include at least one of a high-frequency oscillation-type grip sensor, a capacitive grip sensor, or a magnetic grip sensor. In another example, the temperature sensor may be used as a grip sensor when the electronic device 301 detects a grip, based on temperature.

Figure 7:
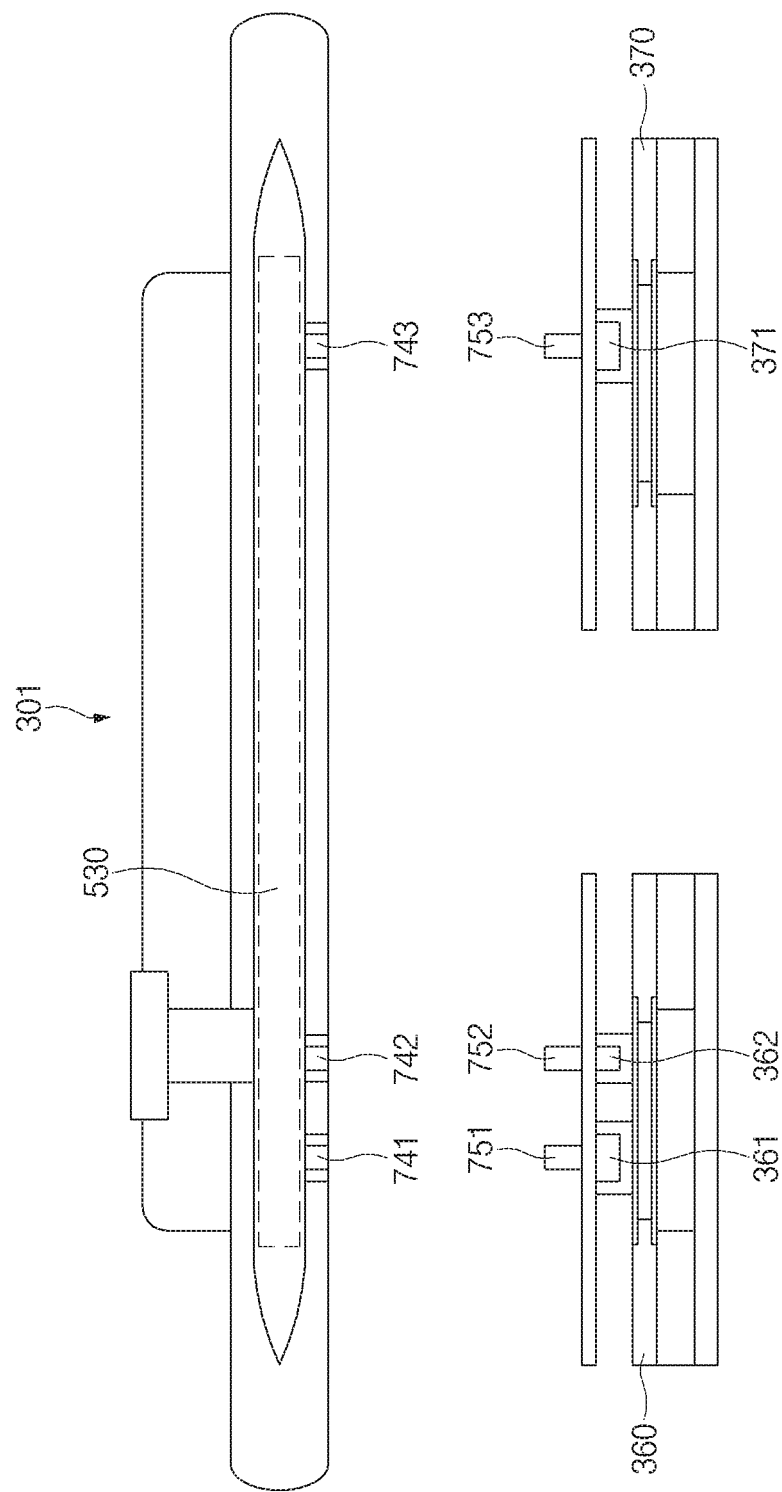
FIG. 7 is a view illustrating a configuration of an electronic device according to an embodiment of the disclosure.

FIG. 7 is a view illustrating a configuration of an electronic device according to yet another embodiment of the disclosure.

Referring to FIG. 7, the electronic device 301 may include at least one of the first pad 360 or the second pad 370 that is detachable. The electronic device 301 may include electrode holders 741, 742, and 743 for coupling the controller 530 and the electrodes 361, 362, and 371.

The first electrode 361 may be electrically coupled to the controller 530, based on the combination of a first connector 751 and the first holder 741. According to an embodiment, the second electrode 362 may be electrically coupled to the controller 530, based on the combination of a second connector 752 and the second holder 742. The third electrode 371 may be electrically coupled to the controller 530, based on the combination of a third connector 753 and the third holder 743.

As illustrated in FIG. 7, according to various embodiments of the disclosure, the pads 360 and 370 may be replaceable. For example, each of the pads 360 and 370 may include an adhesive means (e.g., an adhesive pad) for adhesion to the main body of the electronic device 301. The electronic device 301 may obtain different types of biometric information, depending on the types of the pads (the first pad 360 and the second pad 370). For example, the types of the pads (the first pad 360 and the second pad 370) may be determined based on the types of oxidases (e.g., catalysts) with which the first electrode 361, the second electrode 362, and the third electrode 371 are coated.

While the first pad 360 and the second pad 370 in FIG. 7 are separate from each other, the first pad 360 and the second pad 370 may be implemented with one pad formed on the same adhesive layer according to an embodiment.

Figure 8:
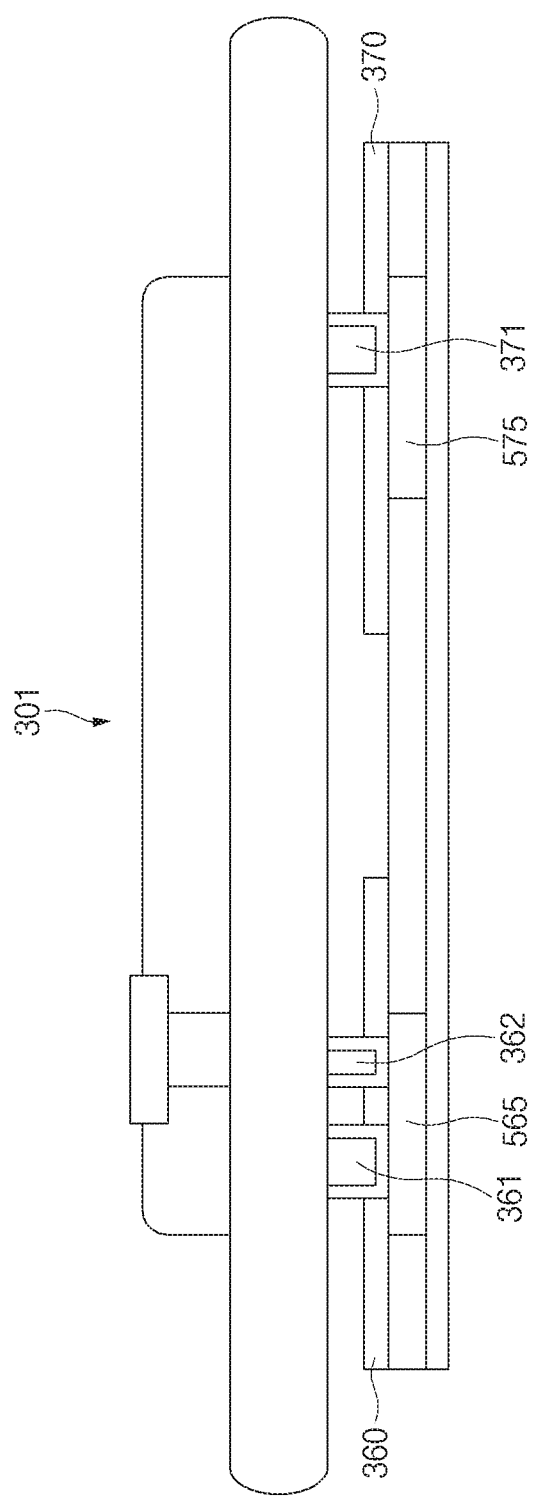
FIG. 8 is a view illustrating a configuration of an electronic device according to an embodiment of the disclosure.

FIG. 8 is a view illustrating a configuration of an electronic device according to an embodiment of the disclosure.

Referring to FIG. 8, according to various embodiments of the disclosure, the electronic device 301 may include a dry electrode. For example, the electronic device 301 using the dry electrode may not include electrolyte-related components (e.g., at least one of the electrolyte conservation layers 564 and 574, the electrolyte layers 563 and 573, or the intermediate pads 551 and 552). Since the electronic device 301 does not include the electrolyte-related components, the first pad 360 and the second pad 370 may have a relatively simple structure. The first electrode 361, the second electrode 362, and the third electrode 371 may be formed of a high-conductive metallic material (e.g., platinum and/or gold) to sense movement of a smaller amount of electric charge than a wet electrode. The electronic device 301 may obtain biometric information (e.g., a degree of fatigue) using an electrolyte due to moisture (e.g., sweat) of a user's skin.

Figure 9:
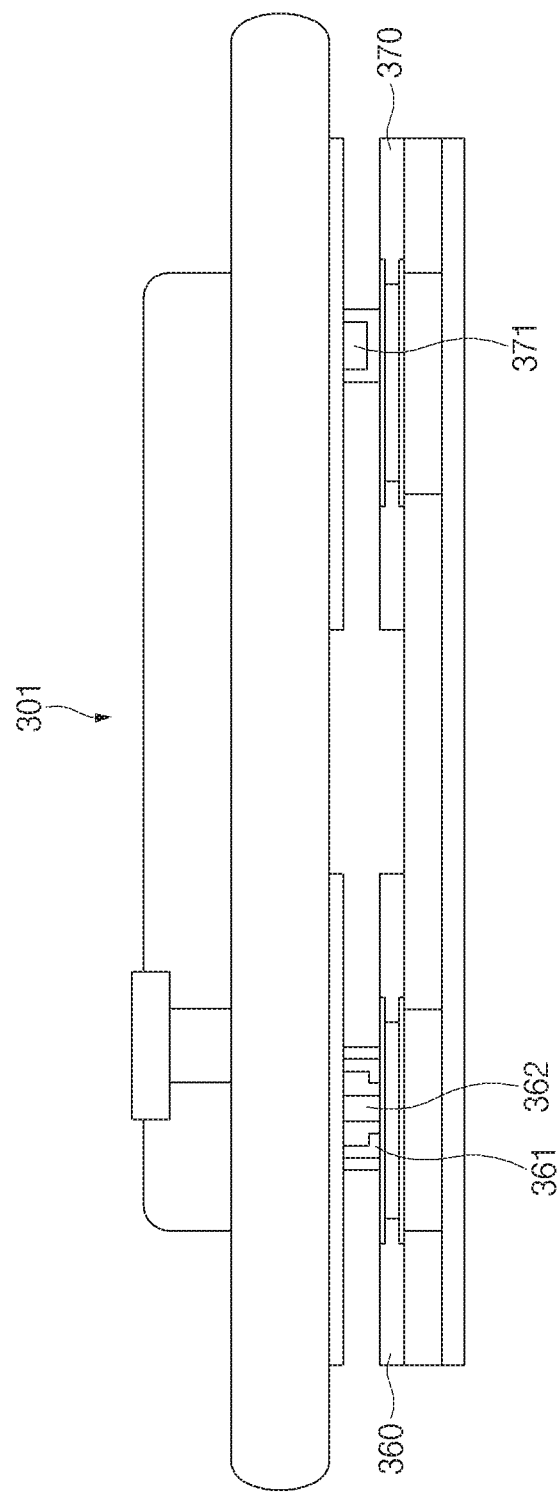
FIG. 9 is a view illustrating a configuration of an electronic device according to an embodiment of the disclosure.

FIG. 9 is a view illustrating a configuration of an electronic device according to an embodiment of the disclosure.

Referring to FIG. 9, the electronic device 301 of FIG. 9 may include the first electrode 361 and the second electrode 362 that have different structures from those illustrated in FIG. 5. For example, descriptions of all components of the electronic device 301 except the first electrode 361 and the second electrode 362 may be referred to by the above description in relation to FIG. 5.

Two electrodes in one pad may have a cylindrical shape. According to an embodiment, the first electrode 361 may have a cylindrical shape, and the second electrode 362 may be located inside the first electrode 361. For example, the second electrode 362 may be a cylindrical electrode. For example, the size of the first pad 360 may be reduced by locating the second electrode 362 inside the first electrode 361. In the case where the second pad 370 includes two electrodes similarly to the second pad 370 of FIG. 6, the electrodes of the second pad 370 may be implemented similarly to the first electrode 361 and the second electrode 362.

The electronic device 301 and the structures associated with the pads 360 and 370 of the electronic device 301 have been described above with reference to FIGS. 5, 6, 7, 8, and 9. Electrical connection relationships between the electrodes 361, 362, and 371 of the electronic device 301 are described below with reference to FIGS. 10 and 11.

Figure 10:
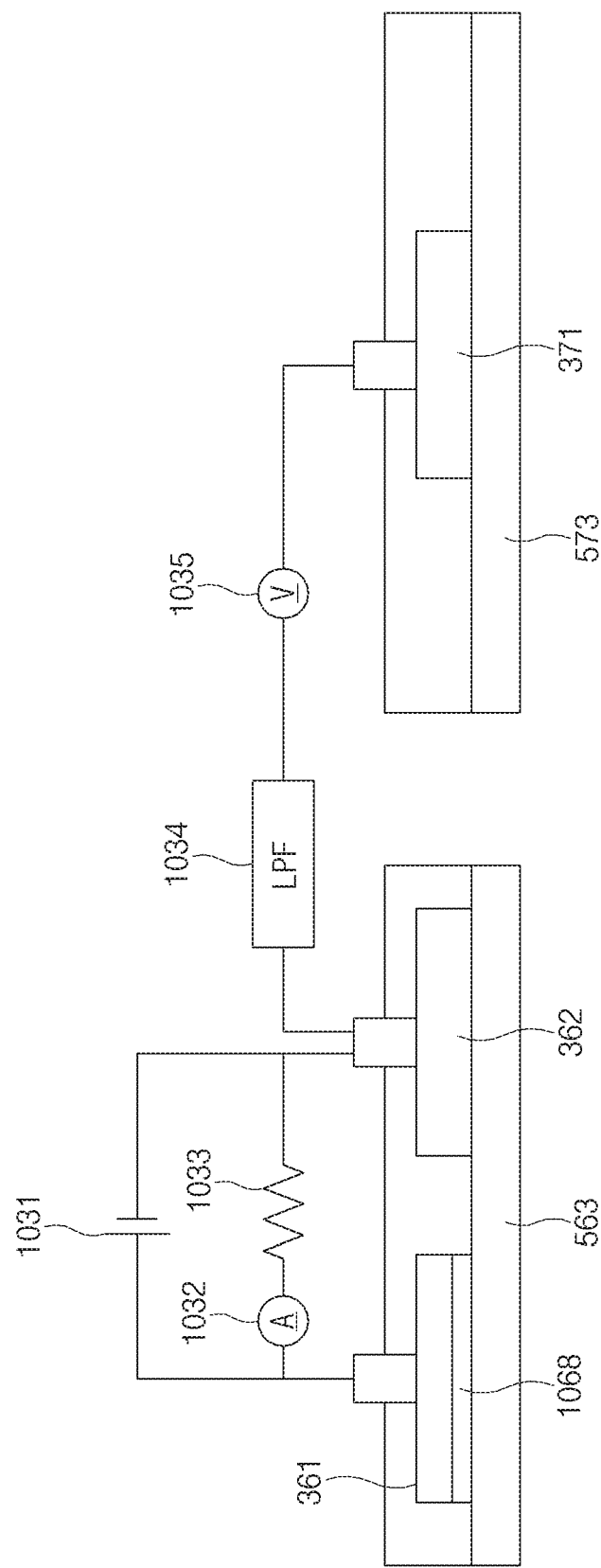
FIG. 10 is a circuit diagram illustrating an electrode configuration of an electronic device according to an embodiment of the disclosure.

FIG. 10 is a circuit diagram illustrating an electrode configuration of an electronic device according to an embodiment of the disclosure.

Referring to FIG. 10, the first electrode 361 may include a coating layer 1068. The first electrode 361 and the second electrode 362 may be electrically coupled together through the electrolyte layer 563. The first electrode 361 and the second electrode 362 may be coupled to a voltage application means 1031 (e.g., a battery and/or a control circuit) and a current measurement means (e.g., an ammeter 1032 and a resistor 1033).

The third electrode 371 may be coupled with the electrolyte layer 573 and may be electrically coupled with the second electrode 362. According to an embodiment, a voltmeter 1035 may be located between the second electrode 362 and the third electrode 371. According to an embodiment, for an improvement in the accuracy of measured voltage, a LPF 1034 may be located between the second electrode 362 and the third electrode 371.

An electronic device (e.g., the electronic device 301) may measure ECG, based on a voltage difference between the second electrode 362 and the third electrode 371.

The electronic device may measure GSR by applying a specified voltage between the second electrode 362 and the third electrode 371 and measuring an electric current that flows between the second electrode 362 and the third electrode 371. For example, the electronic device may obtain a resistance value, based on the applied voltage and the measured current and may measure GSR, based on the resistance value. In FIG. 10, a path to the third electrode 371 may be formed between the first electrode 361 and the current measurement means 1032 and 1033. The electronic device may include a switch (not illustrated) that is configured to couple the current measurement means 1032 and 1033 and the voltage application means 1031 between the first electrode 361 and the second electrode 362 or between the second electrode 362 and the third electrode 371. For example, the second electrode 362 may operate as a reference electrode for both the first electrode 361 and the third electrode 371. In another example, a separate voltage application means and a separate current measurement means may be coupled between the second electrode 362 and the third electrode 371.

The electronic device may measure a degree of fatigue or blood glucose, based on the quantity of electric charge (e.g., electric current) between the first electrode 361 and the second electrode 362. For example, the electronic device may apply voltage between the first electrode 361 and the second electrode 362 using the voltage application means 1031 and may measure an electric current between the first electrode 361 and the second electrode 362 using the ammeter 1032. The second electrode 362 and/or the third electrode 371 may be formed of a conductive material. For example, the second electrode 362 and/or the third electrode 371 may be formed of at least one of a metallic material (e.g., platinum, gold, silver, silver chloride, copper, or stainless steel), a conductive polymer (e.g., polyacetylene, polypyrrole, polythiophene, polyphenylene, polyphenyl, or PEDOT), or a transparent conductive material (e.g., ITO, AZO, SnO, or FTO). The first electrode 361 may be implemented with an electrode having a conductive surface coated with a catalyst (e.g., LOx) for reaction with lactic acid. In another example, the first electrode 361 may be implemented with an electrode having a conductive surface coated with a catalyst (e.g., GOx) for reaction with glucose. The electrolyte layers 563 and 573 may contain a liquid component and/or a conductive material. For example, the electrolyte layers 563 and 573 may contain various ions such as a sodium ion and/or a chloride ion.

Figure 11:
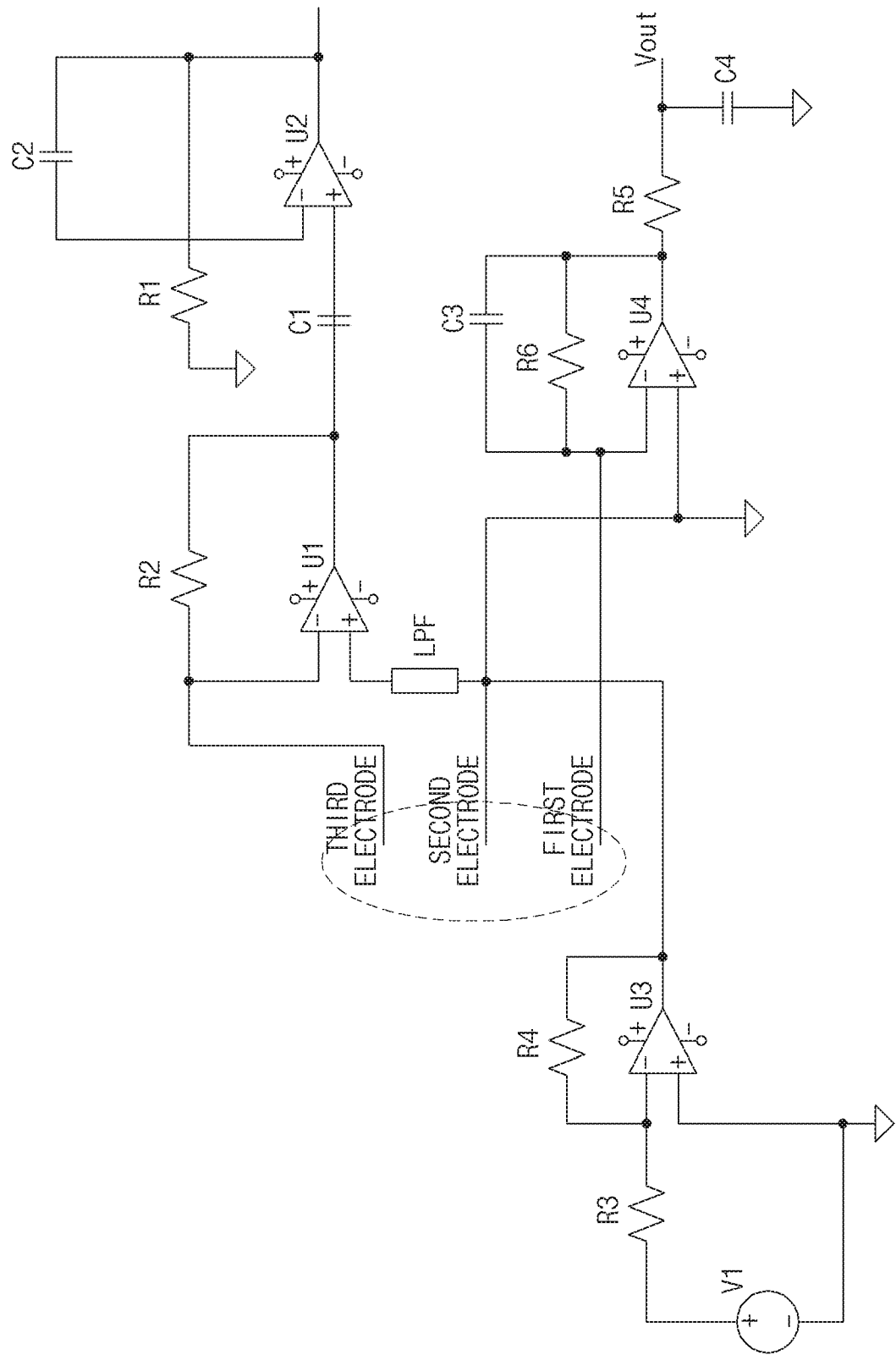
FIG. 11 is a circuit diagram illustrating an electronic device according to an embodiment of the disclosure.

FIG. 11 is a circuit diagram illustrating an electronic device according to an embodiment of the disclosure.

FIG. 11 is a circuit diagram of an electronic device according to an embodiment of the disclosure (e.g., the electronic device 301) that is capable of simultaneously measuring a degree of fatigue (or blood glucose) and ECG.

A power source V1, an amplification unit R3, R4, and U3, and a band pass filter unit C3, R6, U4, R5, and C4 may be located between a first electrode (e.g., the first electrode 361) and a second electrode (e.g., the second electrode 362). For example, the electronic device may measure a degree of fatigue (or blood glucose) by applying voltage between the first electrode and the second electrode and measuring voltage Vout by the quantity of electric charge.

An amplification unit R2 and U1 and a band pass filter unit C1, R1, C2, and U2 may be located between the second electrode and a third electrode (e.g., the third electrode 371). The electronic device may measure ECG by measuring voltage between the second electrode and the third electrode (e.g., the third electrode 371).

According to an embodiment of the present disclosure, a LPF may be coupled to the second electrode to simultaneously measure a degree of fatigue (using the first electrode and the second electrode) and ECG (using the second electrode and the third electrode). According to another embodiment, the second electrode may be sequentially coupled with the first electrode or the third electrode. For example, the second electrode may be coupled with the first electrode or the third electrode through a switching means. The switching means may alternately couple the second electrode with the first electrode or the third electrode every specified time by a timer. For example, the timer may be controlled by a polling or interrupt method, based on a system clock or an external clock.

Figure 12:
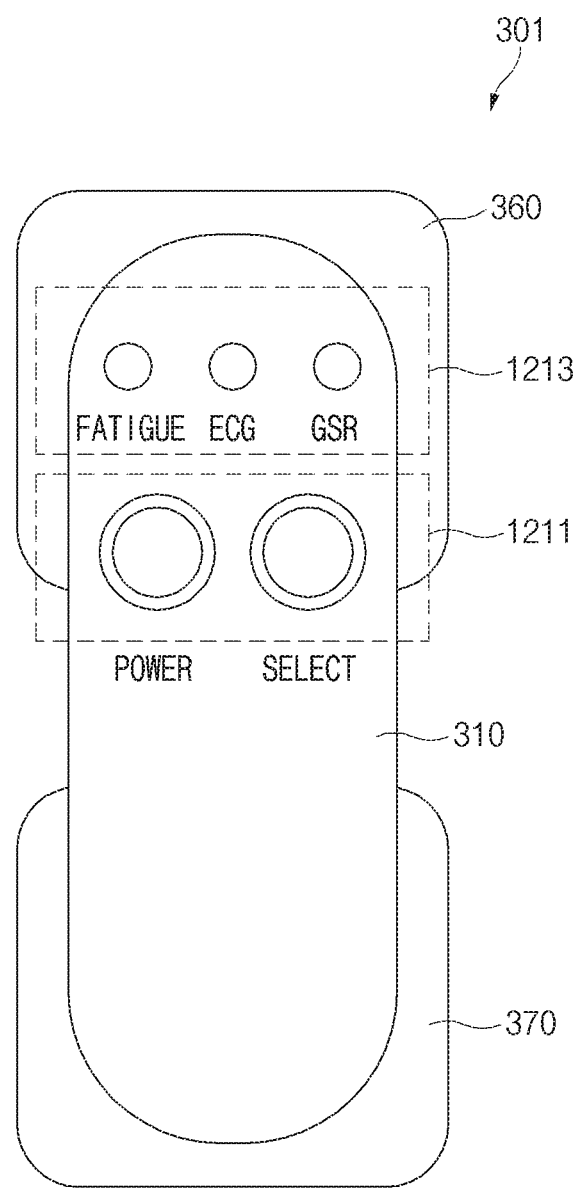
FIG. 12 is a top view illustrating an electronic device according to an embodiment of the disclosure.

FIG. 12 is a top view illustrating an electronic device according to an embodiment of the disclosure.

Referring to FIG. 12, the electronic device 301 may include the upper body 310, the first pad 360, and the second pad 370.

The upper body 310 may include a button unit 1211. For example, the button unit 1211 may include a first button for controlling the power of the pads 360 and 370 and/or the electronic device 301 and a second button for selecting a measurement mode. For example, the electronic device 301 may measure second biometric information (e.g., ECG) or third biometric information (e.g., GSR), based on an input to the second button. In another example, the electronic device 301 may measure first biometric information (e.g., a degree of fatigue or blood glucose), the first and second biometric information, or the first and third biometric information, based on an input to the second button. For example, the electronic device 301 may select a measurement mode (e.g., select biometric information to be measured), based on the number of inputs to the second button or input time for the second button. The configuration of the button unit 1211 illustrated in FIG. 12 is illustrative, and the user interface of the electronic device 301 is not limited thereto. Furthermore, the electronic device 301 may receive a user input from an external electronic device (e.g., the external electronic device 202 of FIG. 2).

The upper body 310 may include a display unit 1213 (e.g., the display device 260 of FIG. 2). For example, the display unit 1213 may include a plurality of LEDs. The electronic device 301 may turn on each LED to display information about the current measurement mode. For example, the electronic device 301 may turn on/off at least one LED to provide notification to a user. The configuration of the display unit 1213 illustrated in FIG. 12 is illustrative, and the display unit 1213 of the electronic device 301 is not limited thereto. For example, the display unit 1213 may include a display.

Hereinabove, the components and operations of the electronic device have been described with reference to FIGS. 1 to 12. Hereinafter, a method of displaying biometric information measured by an electronic device will be described with reference to FIG. 13.

Figure 13:
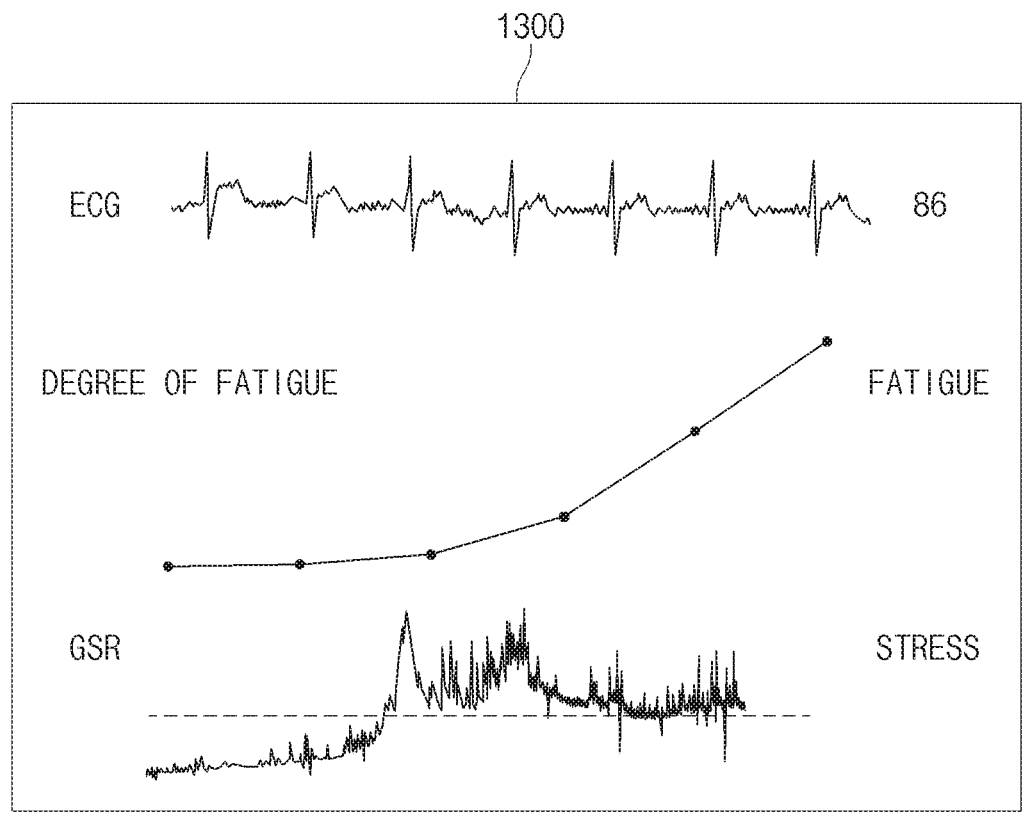
FIG. 13 is a view illustrating a method of displaying biometric information according to an embodiment of the disclosure.

FIG. 13 is a view illustrating a method of displaying biometric information according to an embodiment of the disclosure.

Referring to FIG. 13, an example of a user interface 1300 that indicates measured biometric information is illustrated. For example, the user interface 1300 may include text (e.g., a number or a status) and/or a graphic element (e.g., a graph) for displaying the measured biometric information according to an embodiment of the disclosure.

An electronic device (e.g., the electronic device 201 of FIG. 2) may display a user interface (e.g., the user interface 1300) that indicates the measured biometric information, on a display device (e.g., the display device 260 of FIG. 2). For example, the electronic device may obtain raw data using a sensor module (e.g., the sensor module 276 of FIG. 2) and may display a graphic element (e.g., a graph) on the display device using the raw data. The electronic device may determine a heart rate, a fatigue status (e.g., normal, tired, or very tired), and/or a stress status (e.g., normal, stressed, or very stressed), based on the obtained raw data and may display the heart rate, the fatigue status, and/or the stress status on the display device.

The electronic device may transmit the measured biometric information to an external electronic device (e.g., the external electronic device 202 of FIG. 2) to display, on a display of the external electronic device, a user interface (e.g., the user interface 1300) that indicates the biometric information. For example, the electronic device may obtain raw data using the sensor module (e.g., the sensor module 276) and may transmit the raw data to the external electronic device. In another example, the electronic device may transmit raw data and/or information (e.g., a heart rate, a fatigue status, and/or a stress status) determined based on the raw data, to the external electronic device.

Figure 14:
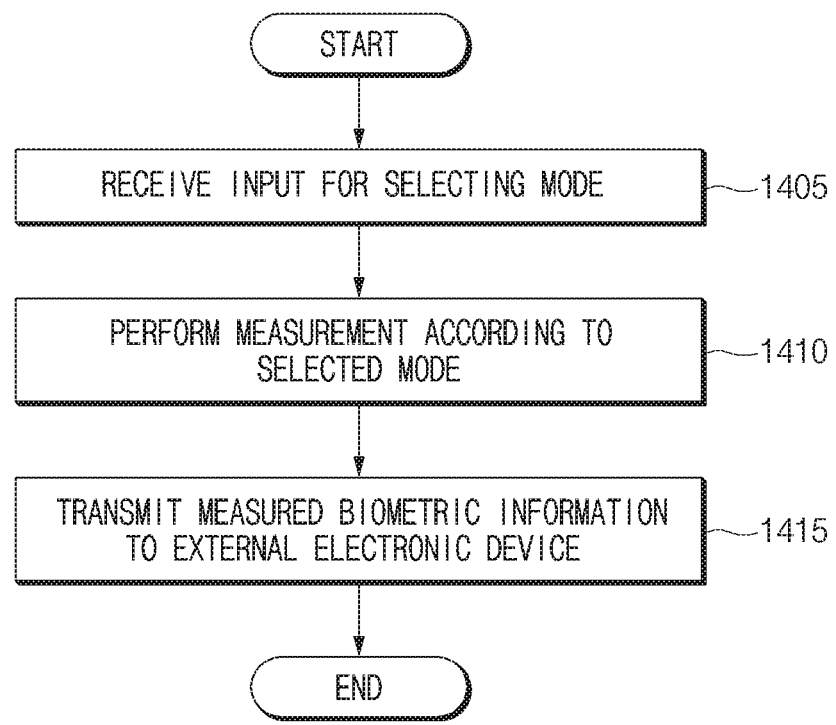
FIG. 14 is a flowchart illustrating a measurement method according to an embodiment of the disclosure.

FIG. 14 is a flowchart illustrating a measurement method according to an embodiment of the disclosure.

Referring to FIG. 14, in operation 1405, the processor 220 of the electronic device 201 may receive an input for selecting a mode. For example, the processor 220 may be turned on in response to an input to a power button and may receive the mode selection input. The processor 220 may receive the mode selection input through a user interface (e.g., the button unit 1211), or may receive the mode selection input from an external electronic device (e.g., the external electronic device 202 of FIG. 2).

Operation 1405 may be omitted. For example, the processor 220 may be configured to measure specified biometric information when the electronic device 201 is turned on.

In operation 1410, the processor 220 may measure biometric information according to a measurement mode selected (or a measurement mode specified) based on the mode selection input. As described above, the processor 220 may substantially simultaneously measure a plurality of biometric information. For example, the processor 220 may obtain the plurality of biometric information at the same time or within a specified time interval. The biometric information may be measured as described above with reference to FIGS. 2 to 11.

In operation 1415, the processor 220 may transmit the measured biometric information to the external electronic device 202 via the communication circuit 290. For example, the processor 220 may transmit the biometric information to the external electronic device 202 every specified period or aperiodically.

Figure 15:
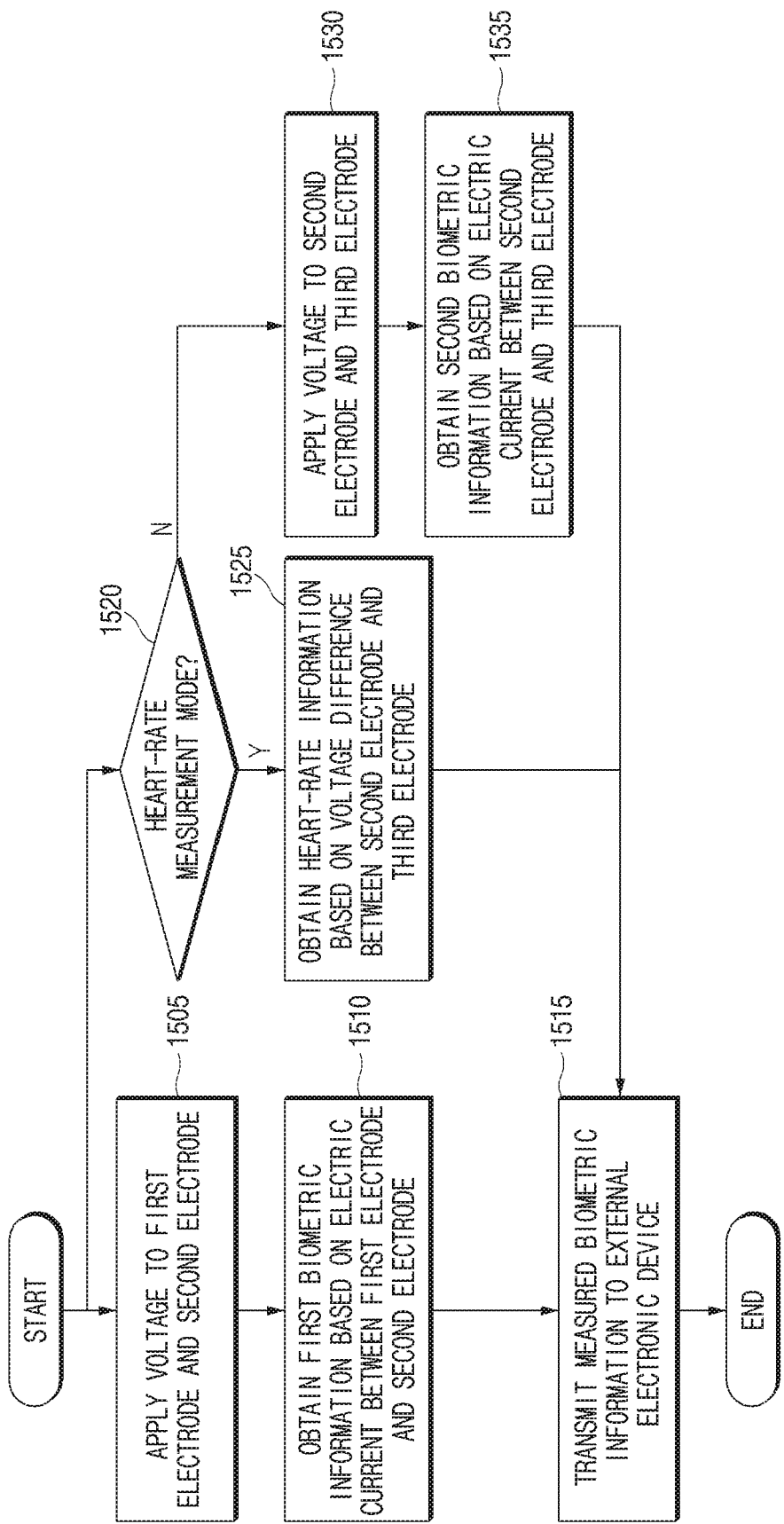
FIG. 15 is a flowchart illustrating a method of measuring various biometric information according to an embodiment of the disclosure.

FIG. 15 is a flowchart illustrating a method of measuring various biometric information according to an embodiment of the disclosure.

Operations of FIG. 15, which will be described below, may be performed after an electronic device (e.g., the electronic device 201 of FIG. 2) is turned on by a power button.

Referring to FIG. 15, in operation 1505, the processor 220 of the electronic device 201 may apply a specified voltage (e.g., about 0.5 V to about 2 V) to a first electrode (e.g., the first electrode 361 of FIG. 3) and a second electrode (e.g., the second electrode 362 of FIG. 3) of the sensor module 276. For example, the processor 220 may apply the specified voltage, based on a power input or a measurement mode selection input. The processor 220 may perform operation 1505 when a grip sensor detects that the electronic device 201 is attached to a user's skin.

In operation 1510, the processor 220 may measure first biometric information (e.g., a degree of fatigue or blood glucose), based on the quantity of electric charge (e.g., electric current) between the first electrode 361 and the second electrode 362. For example, the type of the first biometric information may be determined based on the type of oxidase contained in the first electrode 361. The type of the first biometric information may be changed by changing a pad (e.g., the first pad 360 of FIG. 3) or a patch pad (e.g., the patch pad 460 of FIG. 4) that includes the first electrode 361. The processor 220 may determine the first biometric information to be measured, based on the type of the pad or the patch pad, or based on a user input.

The processor 220 may convert the obtained analog first biometric information into digital first biometric information and may store the first biometric information in the memory 230.

In operation 1515, the processor 220 may transmit the measured first biometric information to an external electronic device (e.g., the external electronic device 202 of FIG. 2). For example, the processor 220 may transmit the biometric information to the external electronic device 202 every specified period or aperiodically. The processor 220 may determine a status (e.g., a degree of fatigue or blood glucose) that corresponds to the first biometric information, based on the measured first biometric information (e.g., an electric current value). For example, the processor 220 may transmit the measured first biometric information and/or a status corresponding to the first biometric information to the external electronic device 202.

In operation 1520, the processor 220 may determine whether the current measurement mode is a heart-rate measurement mode. For example, the processor 220 may determine the current measurement mode, based on a user input or a specified default measurement mode.

In operation 1525, the processor 220 may obtain heart-rate information, based on a voltage difference between the second electrode (e.g., the second electrode 362 of FIG. 3) and a third electrode (e.g., the third electrode 371 of FIG. 3) when it is determined that the current measurement mode is the heart-rate measurement mode. The processor 220 may convert the heart-rate information into digital information and may store the digital information in the memory 230.

In operation 1530, according to various embodiments, the processor 220 may apply voltage to the second electrode 362 and the third electrode 371 when it is determined that the current measurement mode is not the heart-rate measurement mode. In operation 1535, the processor 220 may measure GSR by measuring an electric current between the second electrode 362 and the third electrode 371 while the voltage is being applied. According to an embodiment, the processor 220 may convert the GSR into digital information and may store the digital information in the memory 230.

Figure 16:
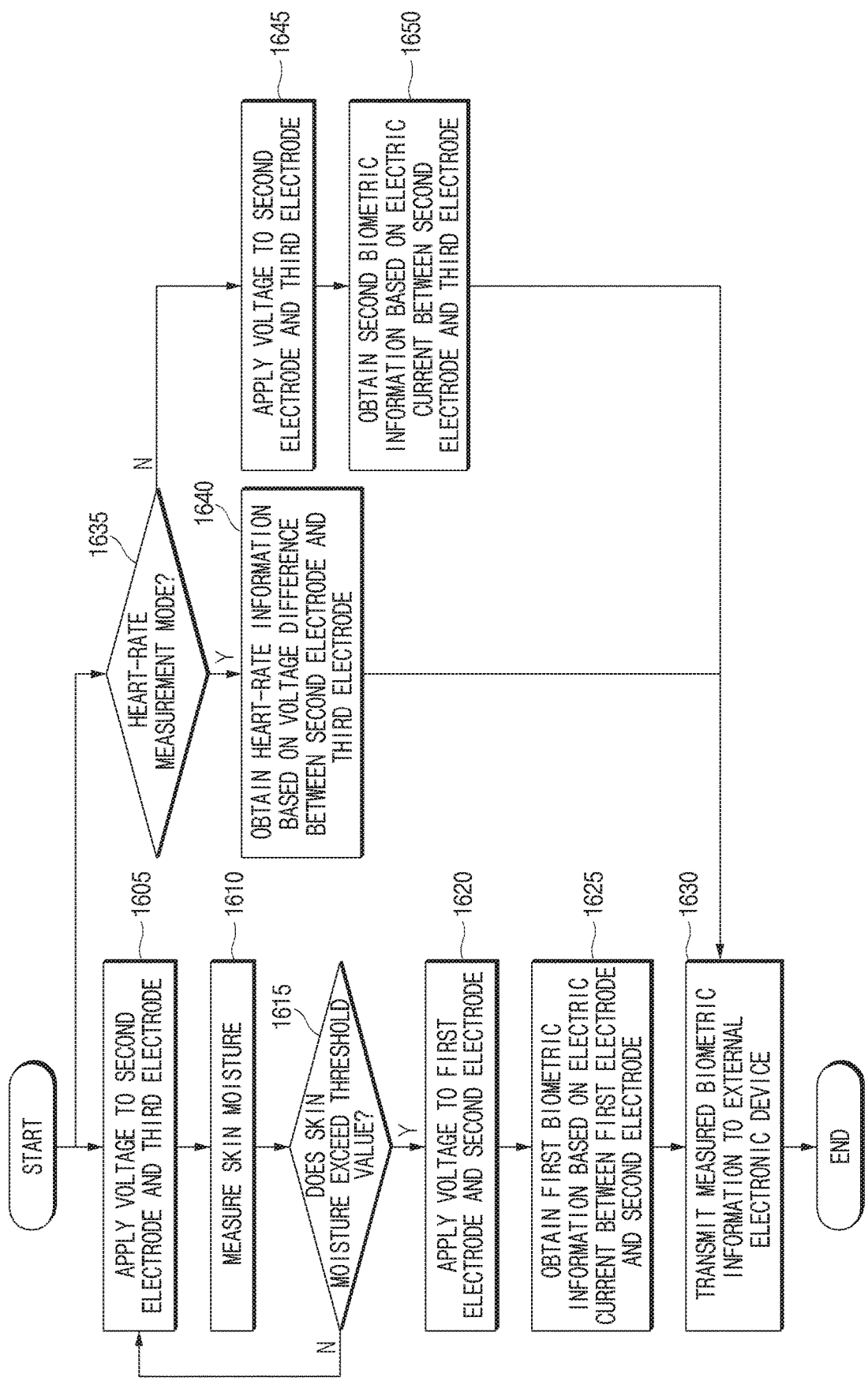
FIG. 16 is a flowchart illustrating a method of measuring various biometric information according to an embodiment of the disclosure.

FIG. 16 is a flowchart illustrating a method of measuring various biometric information according to another embodiment of the disclosure.

Operations of FIG. 16, which will be described below, may be performed after an electronic device (e.g., the electronic device 201 of FIG. 2) is turned on by a power button.

For example, lactic acid or glucose may react with an oxidase (e.g., LOx or GOx) of a first electrode (e.g., the first electrode 361 of FIG. 3) to measure first biometric information (e.g., a degree of fatigue or blood glucose). A predetermined amount of moisture (e.g., sweat) may be required for the reaction of the lactic acid or the glucose with the oxidase. According to an embodiment, the electronic device 201 may measure the first biometric information, based at least on skin moisture.

Referring to FIG. 16, in operation 1605, the processor 220 may apply a specified voltage (e.g., about 0.5 V to about 2 V) to a second electrode (e.g., the second electrode 362 of FIG. 3) and a third electrode (e.g., the third electrode 371 of FIG. 3). In operation 1610, the processor 220 may measure skin moisture. For example, the processor 220 may measure the skin moisture by measuring resistance and/or an electric current between the second electrode 362 and the third electrode 371 by using the voltage applied between the second electrode 362 and the third electrode 371.

In operation 1615, the processor 220 may determine whether the skin moisture exceeds a specified threshold value. The processor 220 may measure the skin moisture every specified period until the skin moisture exceeds the specified threshold value. The processor 220 may measure the first biometric information (e.g., a degree of fatigue or blood glucose) when specified skin moisture is satisfied.

Descriptions of operations 1620, 1625, and 1630 may be referred to by the descriptions of operations 1505, 1510, and 1515. Furthermore, descriptions of operations 1635, 1640, 1645, and 1650 may be referred to by the descriptions of operations 1520, 1525, 1530, and 1535.

Figure 17:
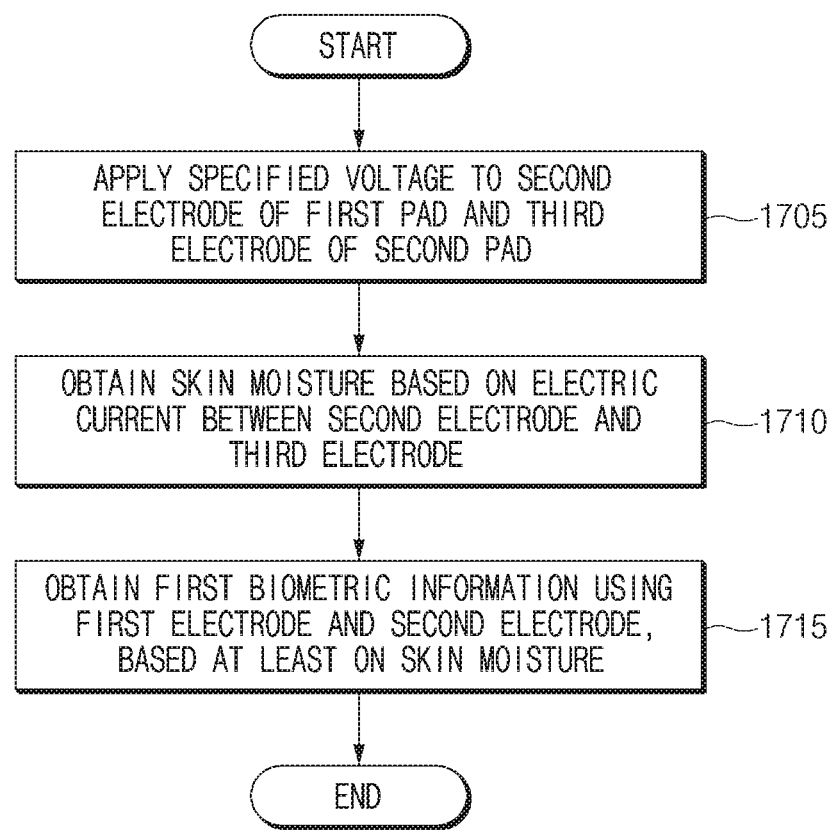
FIG. 17 is a flowchart illustrating a method of obtaining biometric information based on skin moisture according to an embodiment of the disclosure.

FIG. 17 is a flowchart illustrating a method of obtaining biometric information based on skin moisture according to an embodiment of the disclosure.

Operations of FIG. 17, which will be described below, may be performed after an electronic device (e.g., the electronic device 201 of FIG. 2) is turned on by a power button.

Referring to FIG. 17, in operation 1705, according to various embodiments, the processor 220 of the electronic device 201 may apply a specified voltage (e.g., about 0.5 V to about 2 V) to a second electrode (e.g., the second electrode 362 of FIG. 3) and a third electrode (e.g., the third electrode 371 of FIG. 3). In operation 1710, the processor 220 may obtain skin moisture, based on an electric current generated between the second electrode 362 and the third electrode 371 by the applied voltage. For example, the quantity of electric current between the second electrode 362 and the third electrode 371 may be increased as the skin moisture (e.g., sweat) of a wearer of the electronic device 201 increases. The processor 220 may obtain the skin moisture by measuring the quantity of electric current between the second electrode 362 and the third electrode 371.

In operation 1715, the processor 220 may obtain first biometric information (e.g., a degree of fatigue) using a first electrode (e.g., the first electrode 361 of FIG. 3) and the second electrode 362, based at least on the skin moisture. For example, the first electrode 361 may be coated with a catalyst associated with the first biometric information. For example, the processor 220 may obtain the first biometric information when the quantity of skin moisture is beyond a specified range. For example, the processor 220 may obtain the first biometric information by applying a specified voltage between the first electrode 361 and the second electrode 362 and obtaining an electric current between the first electrode 361 and the second electrode 362.

The operations of the electronic device described above with reference to FIGS. 14 to 17 are illustrative. The above-described operations may be combined with the configuration and the operations of the electronic device described above with reference to FIGS. 1 to 13.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   at least one communication circuit;
   a first pad including a first electrode and a second electrode, the first electrode being coated with a catalyst associated with first biometric information, the first electrode and the second electrode having a cylindrical shape, and the second electrode being located inside the first electrode;
   a second pad including at least a third electrode; and
   a processor configured to control the at least one communication circuit, the first pad, and the second pad,
   wherein the processor is configured to:
       obtain the first biometric information, based at least on an electric current induced by applying a first specified voltage between the first electrode and the second electrode,
       obtain second biometric information, based at least on a voltage difference between the second electrode and the third electrode, and
       obtain third biometric information based on an electric current between the second and third electrodes induced by applying second specified voltage between the second electrode and the third electrode.

2. The electronic device of claim 1, wherein the processor is further configured to obtain the first biometric information by using the first electrode as a working electrode and the second electrode as a reference electrode and a counter electrode.

3. The electronic device of claim 1,
wherein the first biometric information includes at least one of a lactate concentration or a degree of fatigue, and
wherein the catalyst includes a lactate oxidase.

4. The electronic device of claim 1,
wherein the first biometric information includes at least one of a glucose concentration or blood glucose, and
wherein the catalyst includes a glucose oxidase.

5. The electronic device of claim 1, wherein the first pad and the second pad include an electrolyte layer containing an ion-conducting material.

6. The electronic device of claim 1,
wherein the processor is further configured to obtain the second biometric information or the third biometric information, based on a user input, and
wherein the user input is received from an external electronic device via the at least one communication circuit, or is received through a user interface of the electronic device.

7. The electronic device of claim 6,
wherein the second electrode and the third electrode are formed of at least one of a metallic material, a conductive polymer, or a transparent conductive material,
wherein the metallic material includes at least one of platinum, gold, silver, silver chloride, copper, or stainless steel,
wherein the conductive polymer includes at least one of polyacetylene, polypyrrole, polythiophene, polyphenylene, polyphenyl, or poly(3,4-ethylenedioxythiophene) (PEDOT), and
wherein the transparent conductive material includes at least one of indium tin oxide (ITO), aluminum-doped zinc oxide (AZO), tin(II) oxide (SnO), or fluorine-doped tin oxide (FTO).

8. The electronic device of claim 6, wherein the processor is further configured to transmit at least one of the first biometric information, the second biometric information, or the third biometric information to the external electronic device by using the at least one communication circuit.

9. The electronic device of claim 8,
wherein the at least one communication circuit is configured to provide communication between the electronic device and the external electronic device via a short-range wireless network, and
wherein the short-range wireless network includes at least one of near field communication (NFC), Bluetooth, Bluetooth low energy (BLE), Zigbee, or Z-wave.

10. The electronic device of claim 1, further comprising:
a low pass filter (LPF),
wherein the LPF is disposed between the second electrode and the third electrode.

11. The electronic device of claim 1,
wherein the processor is further configured to obtain the first biometric information when a specified condition is satisfied, and
wherein the specified condition includes skin moisture that is greater than or equal to a specified value.

12. The electronic device of claim 11, wherein the third biometric information includes the skin moisture.

13. The electronic device of claim 1,
wherein the second pad further includes a fourth electrode, and
wherein the processor is further configured to sense at least one of temperature, humidity, or grip by using the fourth electrode.

14. The electronic device of claim 1, wherein the first pad and the second pad are detachable.

15. The electronic device of claim 1,
wherein the processor is further configured to provide notification when the first biometric information satisfies a first condition specified or the second biometric information satisfies a second condition specified,
wherein the first condition includes the first biometric information outside a first range specified, and
wherein the second condition includes the second biometric information outside a second range specified.

16. The electronic device of claim 15, wherein the processor is further configured to provide the notification through a display device of the electronic device or by using an external electronic device.

* * * * *